(12) United States Patent
Martel et al.

(10) Patent No.: US 10,209,194 B2
(45) Date of Patent: Feb. 19, 2019

(54) RAMAN SCATTERING NANOPROBES

(71) Applicant: VALORISATION-RECHERCHE, LIMITED PARTNERSHIP, Montreal (CA)

(72) Inventors: Richard Martel, Montreal (CA); Nathalie Y-Wa Tang, Saint-Leonard (CA); Francois Raymond, Deux-Montagnes (CA); Janie Cabana, Riviere-Beaudette (CA); Marc-Antoine Nadon, Montreal (CA)

(73) Assignee: VALORISATION-RECHERCHE, LIMITED PARTNERSHIP, Montreal (CA)

( * ) Notice: Subject to any disclaimer, the term of this patent is extended or adjusted under 35 U.S.C. 154(b) by 163 days.

(21) Appl. No.: 15/189,881

(22) Filed: Jun. 22, 2016

(65) Prior Publication Data
US 2016/0299082 A1    Oct. 13, 2016

Related U.S. Application Data

(62) Division of application No. 13/985,018, filed as application No. PCT/CA2012/050099 on Feb. 20, 2012, now Pat. No. 9,395,305.

(30) Foreign Application Priority Data

Feb. 18, 2011 (CA) .................................. 2731892

(51) Int. Cl.
| | |
|---|---|
| *G01N 21/00* | (2006.01) |
| *G01N 21/65* | (2006.01) |
| *B82Y 15/00* | (2011.01) |

(52) U.S. Cl.
CPC ........... *G01N 21/658* (2013.01); *G01N 21/65* (2013.01); *B82Y 15/00* (2013.01);
(Continued)

(58) Field of Classification Search
CPC ..................................................... G01N 21/658
(Continued)

(56) References Cited

U.S. PATENT DOCUMENTS

| | | |
|---|---|---|
| 6,875,412 B2 | 4/2005 | Margrave et al. |
| 7,256,886 B2 | 8/2007 | Cullum et al. |

(Continued)

FOREIGN PATENT DOCUMENTS

| | | |
|---|---|---|
| JP | 2005-533246 | 11/2005 |
| JP | 2010-203875 | 9/2010 |

(Continued)

OTHER PUBLICATIONS

Office Action dated Dec. 10, 2015, in corresponding Japanese Application No. 2013-553754 (2 pages).
(Continued)

*Primary Examiner* — Christopher Adam Hixson
*Assistant Examiner* — Emily R. Berkeley
(74) *Attorney, Agent, or Firm* — Hovey Williams LLP

(57) ABSTRACT

A Raman scattering probe, and a method of making such a probe, uses a capsule of nanometric size, such as a nanotube, to which is coupled at least one Raman-active molecule. The Raman-active molecule may be encapsulated in, or attached on the exterior of, the capsule, and exhibits a Raman scattering response when the probe is illuminated by an excitation light beam. A functionalization chemical group that is attached to an exterior of the capsule provides a connection between the capsule and a target material. This functionalization may include a generic chemical functionalization that bonds with any of a plurality of secondary chemical groups each of which bonds directly with a different target. A method of using the probe for Raman spectroscopy or Raman imaging is also provided.

11 Claims, 17 Drawing Sheets

(52) U.S. Cl.
CPC ............... *G01N 2201/068* (2013.01); *G01N 2201/06113* (2013.01); *Y10S 977/954* (2013.01); *Y10S 977/958* (2013.01); *Y10T 156/10* (2015.01)

(58) Field of Classification Search
USPC ........................................................ 436/164
See application file for complete search history.

(56) References Cited

U.S. PATENT DOCUMENTS

| | | | |
|---|---|---|---|
| 7,301,624 | B2 | 11/2007 | Talley et al. |
| 7,586,601 | B2 | 9/2009 | Ebstein |
| 2005/0147977 | A1 | 7/2005 | Koo et al. |
| 2005/0147981 | A1 | 7/2005 | Yamakawa et al. |
| 2005/0148100 | A1 | 7/2005 | Su et al. |
| 2005/0181409 | A1 | 8/2005 | Park et al. |
| 2008/0241262 | A1 | 10/2008 | Lee et al. |
| 2009/0166560 | A1 | 7/2009 | Dai et al. |
| 2010/0074845 | A1 | 3/2010 | Gambhir et al. |

FOREIGN PATENT DOCUMENTS

| | | |
|---|---|---|
| WO | 2004/007767 A2 | 1/2004 |
| WO | 2009142604 A1 | 11/2009 |

OTHER PUBLICATIONS

Chen, Zhuo, et al, "Protein microarrays with carbon nanotubes as multicolor Raman labels", Nature Biotechnology, 2008, vol. 26, pp. 1285-1292 (9 pages).
Kazuhiro Yanagi, et al., Photosensitive Function of Encapsulated Dye in Carbon Nanotubes, J. Am. Chem. Soc. 2007, 129, 4992-4997.
Bohn, et al. Estimating the Raman Cross Sections of Single Carbon Nanotubes, ACS Nano, American Chemical Society, 2010, p. 3466-3470, vol. 4, No. 6.
Martel, Sorting Carbon Nanotubes for Electronics, ACS nano, American Chemical Society, 2008, p. 2195-2199, vol. 2, No. 11.
De La Zerda et al. Carbon nanotubes as photoacoustic molecular imaging agents in living mice, Nat Nanotechnol, 2008, 3(9): p. 557-562.
Jorio et al., Structural (n,m) Determination of Isolated Single-Wall Carbon Nanotubes by Resonant Raman Scattering, Physical Review Letters, vol. 86, No. 6, 2001, p. 1118-1121.
Saito et al, Using a nano light source to investigate small-scale composite materials, 2008, Spie, 1070 p. 1-2.
Kim et al., Aptamer-Mediated Surface-Enhanced Raman Spectroscopy Intensity Amplification, Nano Letters 10, American Chemical Society, 2010, p. 4181-4185.
Loi et al, Encapsulation of Conjugated Oligomers in Single-Walled Carbon Nanotubes: Towards Nanohybrids for Photonic Devices, Advanced Materials, 22, 2010 p. 1-5.
Loi et al., Encapsulation of Conjugated Oligomers in Single Wall Carbon Nanotubes: Towards Nano-Hybrids for Photonic Devices, Supplementary Information, Advanced Materials, 2010, 5 pages.
Schulte et al., Assembly of Cobalt Phthalocyanine Stacks inside Carbon Nanotubes, Advanced Materials, 19, 2007, p. 3312-3316.
Yanagi et al, Highly Stabilized β-Carotene in Carbon Nanotubes, 2006, Advanced Materials, 18, p. 437-441.
Khlobystov et al., Molecules in Carbon Nanotubes, Accounts of Chemical Research, vol. 38, No. 12, 2005, p. 901-909.
Tian et al, Explanding generality of surface-enhanced Raman spectroscopy with borrowing SERS activity strategy, Chem. Commun, The Royal Society of Chemistry, 2007, p. 3514-3534.
Tamayo et al, Design, Synthesis, and Self-assembly of Oligothiophene Derivatives with a Diketopyrrolopyrrole Core, J. Phys. Chem. C 112, American Chemical Society, 2008, p. 5543-15552.
Jeong et al., Polarized Surface Enhanced Raman Scattering from Aligned Silver Nanowire Rafts, J. Phys. Chem. B 108, American Chemical Society, 2004, p. 12724-12728.
Moskovits, Surface-enhanced Raman spectroscopy: a brief retrospective, Journal of Raman Spectroscopy, 36, 2005, p. 485-496.
Yanagi et al., Photosensitive Function of Encapsulated Dye in Carbon Nanotubes, J. Am. Chem. Soc. 9 vol. 129, No. 16, JACS Articles, 2007, p. 4492-4497.
Saito et al., Vibrational Analysis of Organic Molecules Encapsulated in Carbon Nanotubes by Tip-Enhanced Raman Spectroscopy, Japanese Journal of Applied Physics, vol. 45, No. 12, 2006, pp. 9286-9289.
Schulte et al., Encapsulation of cobalt phthalocyanine molecules in carbon nanotubes, Journal of Phyics: Conference Series 100, IPO Publishing, 2008, p. 1-5.
Hebert et al., Investigation of 6T@SWNTs by Cs corrected TEM, MC2009, vol. 3: Materials Science, 2009, p. 381-382.
Liu et al., Imaging the dynamic behaviour of individual retinal chromophores confined inside carbon nanotubes, nature nanotechnology, vol. 2, NaturePublishing Group, 2007, p. 422-425.
Britz et al, Noncovalent interactions of molecules with single walled carbon nanotubes, Chemical Society Reviews, 35, The Royal Society of Chemistry, 2006, p. 637-659.
Kamaras et al, Surface-induced changes in the vibrational spectra of conducting polymer—carbon nanotube hybrid materials, Physica status solidi, B 246, No. 11-12, 2009, p. 2737-2739.
Moura et al., Charge transfer and screening effects in polyynes encapsulated inside single-wall carbon nanotubes, Physical Review B 80, Rapid Communications, The American Physical Society, 2009, p. 161401R 1-4.
Yanagi et al., Light-harvesting function of β-carotene inside carbon nanotubes, Physical Review B 74, The American Physical Society, 2006, p. 155420 1-5.
Abe et al, Light-harvesting function of β-carotene inside carbon nanotubes explored by femtosecond absorption spectroscopy, Physical Review B 77, The American Physical Society, 2008, p. 165436 106.
Berciaud et al, Luminescence Decay and the Absorption Cross Section of Individual Single-Walled Carbon Nanotubes, Physical Review Letters 101, The American Physical Society, 2008, p. 077402 1-4.
Kim et al., Encapsulation and polymerization of acetylene molecules inside a carbon nanotube, Chemical Physics Letters 415, Science Direct, 2005, p. 279-282.
Lee et al, Efficient visible photoluminescence from encapsulation of fluorescent materials inside single-walled carbon nanotubes, Colloids and Surfaces A: Physicochem. Eng. Aspects 313-314, Science Direct, 2008, p. 296-299.
Hermet et al., Polymorphorphism of Crystalline α-Quaterthiophene and α-Sexithiophene: Ab Initio Analysis and Comparison with Inelastic Neutron Scattering Response, J. Phys. Chem A, vol. 109, No. 18, The American Physical Society, 2005, p. 4202-4207.
Liu et al, Circulation and long-term fate of functionalized, biocompatible single-walled carbon nanotubes in mice probed by Raman spectroscopy, PNAS, vol. 105, No. 5, 2008, p. 1410-1415.
Liu et al, Multiplexed Five-Color Molecular Imaging of Cancer Cells and Tumor Tissues with Carbon Nanotube Raman Tags in the Near-Infrared, Nano Research 3, 2010, p. 223-233.
Ntziachristos, Fluorescence Molecular Imaging, Annual Review of Biomedical Engineering, vol. 8, 2006, p. 1-35.
Shim et al., Resonance Raman Cross-sections and Vibronic Analysis of Rhodamine 6G from Broadband Stimulated Raman Spectroscopy, ChemPhysChem 9, Communications, p. 697-699.
Nie et al., Probing Single Molecules and Single Nanoparticles by Surface-Enhanced Raman Scattering, Science vol. 275, 1997, p. 1102-1106.
International Search Report and Written Opinion in corresponding PCT/CA2012/050099 dated Mar. 21, 2012.
Wei Xie et al., Nuclear Targeted Nanoprobe for Single Living Cell Detection by Surface-Enhanced Raman Scattering, Bioconjugate Chem. 2009, 20, 768-773.
Supplemental European Search Report in corresponding European Application Serial No. 12746508.6, dated Oct. 30, 2017.

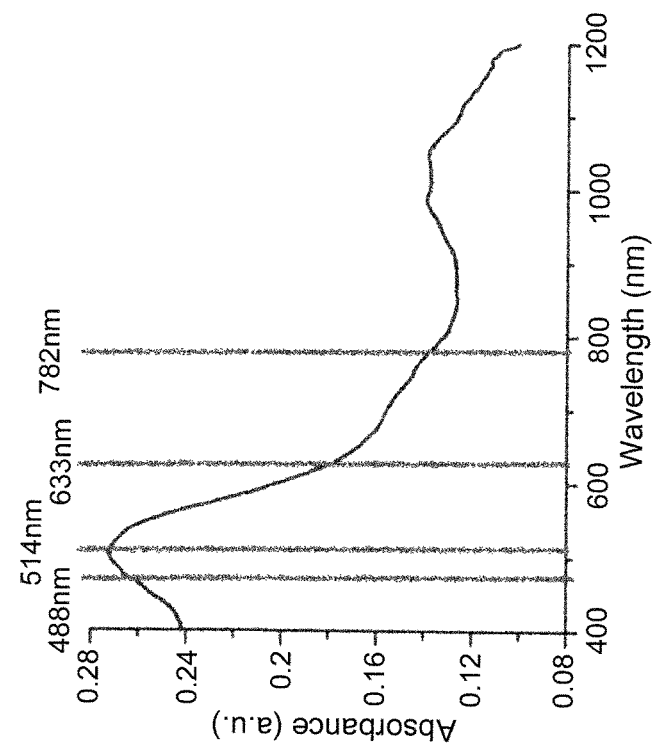
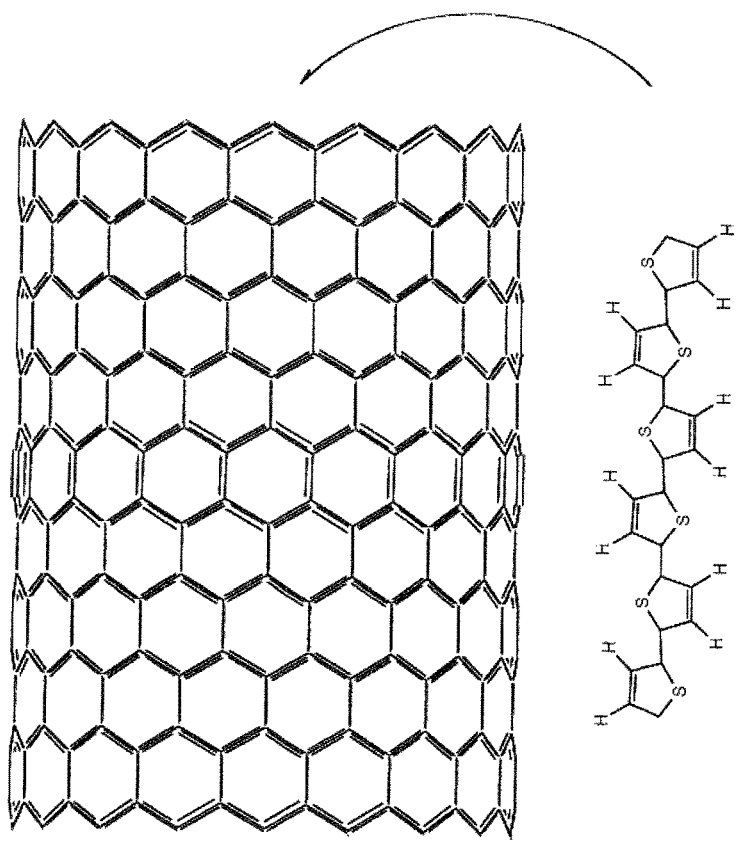
*FIGURE 3B*
*FIGURE 3A*

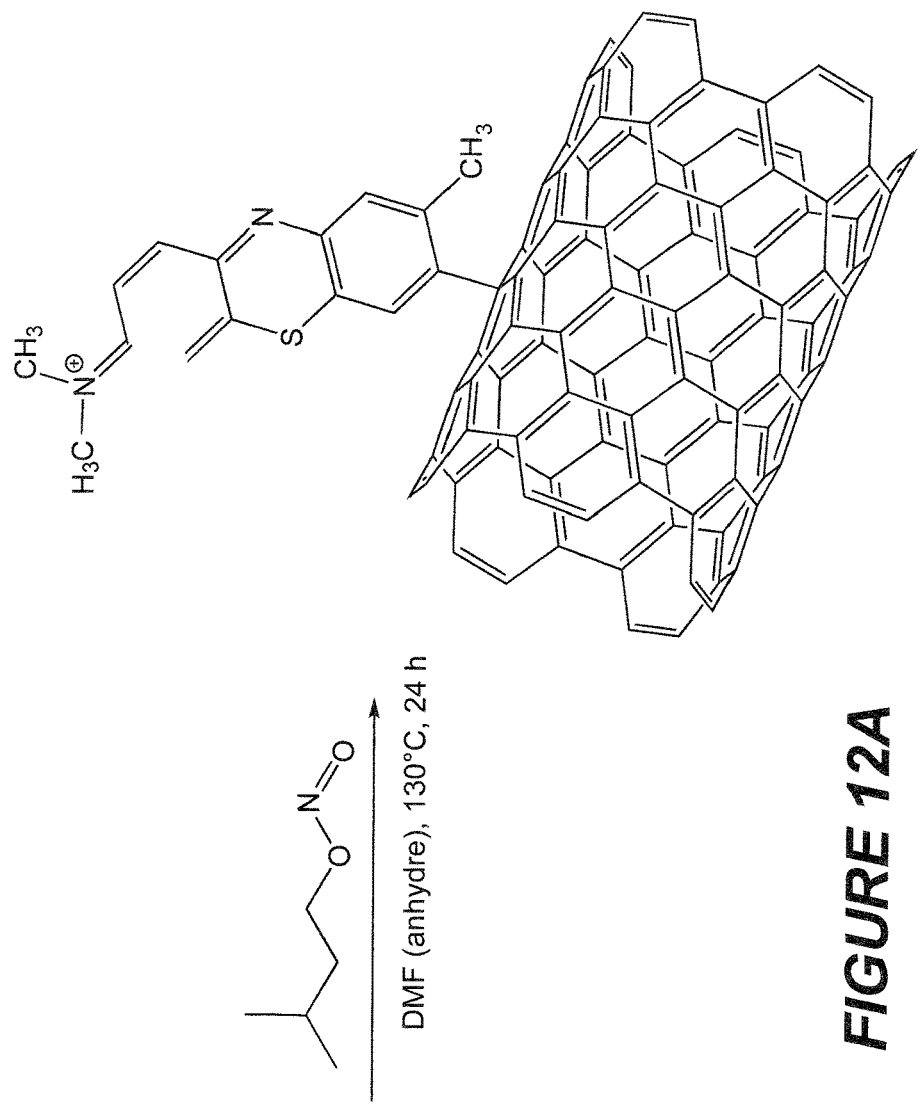
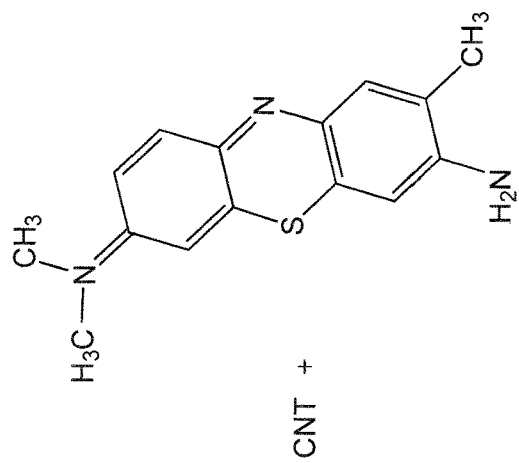
FIGURE 12A

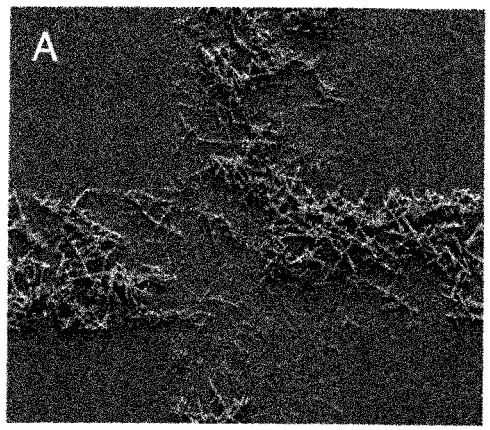
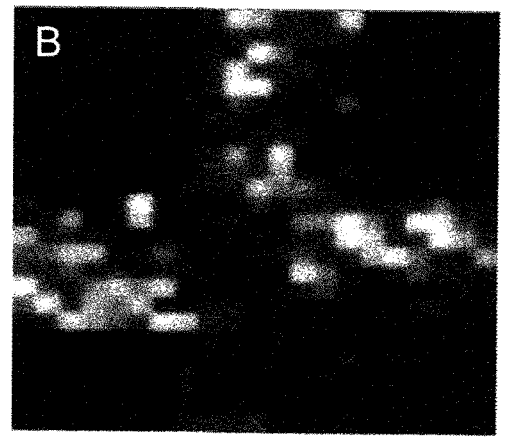
FIGURE 16A  FIGURE 16B
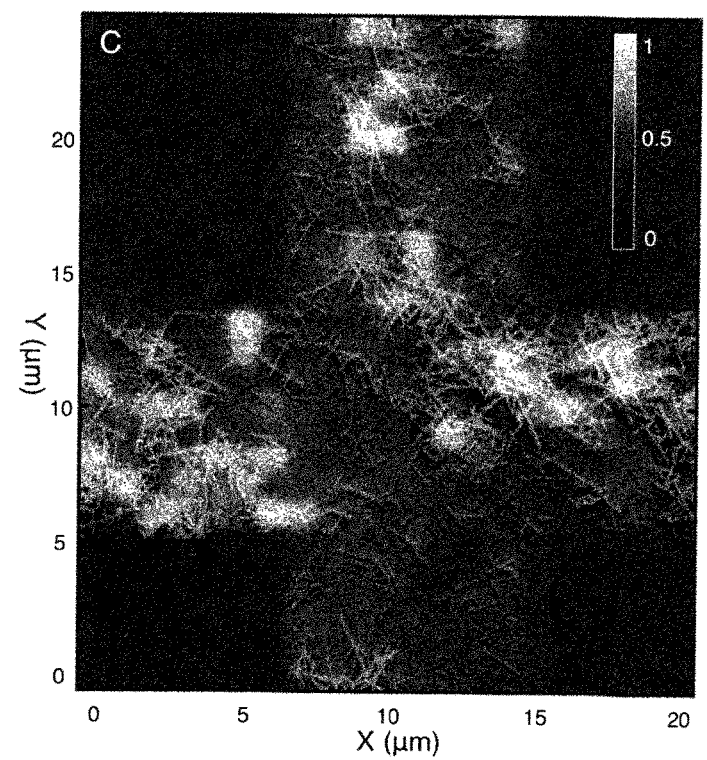
FIGURE 16C

RAMAN SCATTERING NANOPROBES

RELATED APPLICATIONS

The present application is a divisional of U.S. Ser. No. 13/985,018, which is the national stage application under 35 U.S.C. § 371 of International PCT/CA2012/050099, filed 20 Feb. 2012, which claims priority from Canadian Patent Application No. 2,731,892, filed 18 Feb. 2011. The disclosures of the above-referenced applications are hereby incorporated by reference in their entirety.

FIELD OF THE INVENTION

The present invention relates, generally, to the field of nanoscale spectroscopy and imaging and, more specifically, to the preparation and use of nanoscale probes for molecular marking in Raman spectroscopy and imaging.

BACKGROUND OF THE INVENTION

Current contrasting and labelling methods for optical imaging are extensively used in light absorption, optical reflection and molecular fluorescence. Such optical imaging techniques are often used for applications such as medical diagnosis, civil security, mining exploration, etc. Fluorescence labelling is used in many different applications such as, for example, automated DNA sequencing.

Recently, there has been a growing interest in the development of optical imaging techniques in which the high contrast is molecular specific and based on molecular vibrations. The challenge is to obtain an unambiguous molecular detection without loss of sensitivity. Raman spectroscopy is among the most powerful techniques available for the identification and analysis of molecular vibrations, but it lacks sensitivity relative to other spectroscopic techniques. As a result, Raman imaging and the use of Raman molecular probes are rarely found in commercial applications.

Raman Sensitivity

The sensitivity of various imaging techniques can be compared by considering the cross section required to observe light scattering. In Raman spectroscopy, the intensity, I, (in photons/s/cm$^2$) of scattered light for a molecule is proportional to the scattering cross section per molecule $\sigma_R$ and the intensity of the incident light $I_o$, according to the relation $I=\sigma_R I_o$. For Raman spectroscopy, $\sigma_R$ is between $10^{-29}$ and $10^{-32}$ cm$^2$, while the equivalent fluorescence and optical absorption cross sections are on the order of $10^{-19}$ to $10^{-18}$ and $10^{-29}$ to $10^{-32}$ cm$^2$, respectively (S. Nie and S. R. Emory, "Probing Single Molecules and Single Nanoparticles by Surface-Enhanced Raman Scattering", Science 275 1 102-1106 (1997)). There are therefore approximately more than twelve orders of magnitude difference between the relative efficiencies of the Raman process and those of optical absorption or fluorescence. Raman spectroscopy benefits, however, from high laser intensities, which compensate for the low efficiency of the scattering process to make this analytical technique more accessible. Nevertheless, the low sensitivity remains a problem for Raman imaging. In addition, the use of high intensity excitation lasers can alter the samples being examined due to localized heating. In such cases, the acquisition of a Raman image is done by sweeping the light-emitting probe point by point with a reduced intensity to avoid the heating, which makes the acquisition time-consuming and inefficient. Being much more sensitive, fluorescence and absorption/reflection have been heretofore the techniques of choice for optical imaging [V. Ntziachristos, *Fluorescence molecular Imaging*, Annual Review of Biomedical Engineering, Vol. 8: 1-33 (2006)].

Use of Optical Probes for Chemical Analysis

Chemical analysis is possible in absorption and fluorescence spectroscopy, but absorption or fluorescent emission bands are wide and imprecise. However, the optical contrasts in absorption are generally weak for materials with similar transparencies, and most molecules are not or only weakly fluorescent. Thus, it is often necessary to add optical dyes to the samples. There is a wide range of optical dyes or fluorophores available on the market, and these are frequently used as contrast agents or molecular probes. This practice is also commonly used to improve the contrasts in photoacoustic imaging [A. De La Zerda et al. "Carbon nanotubes as photoacoustic molecular imaging agents in living mice" Nat. Nanotechnol. Vol. 3, No. 9, 557-562 (2008)]. Since these contrast agents have very wide absorption or emission bands, it is, however, difficult to mix multiple contrast agents such as these and preserve a clean wavelength signature for each.

On the other hand, a highly specific molecular contrast is possible with Raman and infrared spectroscopy because they provide information on the vibrational transitions of the molecules (from 100 cm$^{-1}$ to 6000 cm$^{-1}$) and present a series of very narrow spectral bands (generally less than 5 cm$^{-1}$). Each molecule or solid possesses a rich spectrum of vibrational transitions, and their Raman and infrared spectra give precisely this information; the vibrational spectrum being somewhat like a "fingerprint" of the molecule.

Raman and infrared absorption are thus very powerful techniques for chemical analysis, but the weakness of each is the strength of the other. Infrared absorption offers a good sensitivity ($\sigma_R \sim 10^{-21}$ cm$^2$) relative to Raman ($\sigma_R \sim 10^{-29}$ cm$^2$), but this efficiency is mitigated by the poor sensitivities of optical detectors in the infrared region. Raman operates instead in the visible range (400-800 nm) where detectors of the type Si CCD are very efficient and sensitive (only a few photons are needed for signal detection). Moreover, the spatial resolution is poor in infrared and excellent in Raman because the resolution limit depends on wavelength (the limit of resolution is $\sim\lambda/2$ according to the Rayleigh criterion), which is relatively long for infrared ($\lambda \sim 30$ µm) and short for Raman ($\lambda=400$-600 nm). Applications using Raman would be ideal, but the problem arises with the cross sections of Raman scattering, which are too weak to be useful in optical imaging or molecular marking.

Amplified Raman Probes

Solutions have been proposed to attempt to improve the sensitivity of molecular detection in Raman scattering.

For example, it has been observed that there can be an amplification of a Raman signal when probe molecules are in proximity to metal particles or rough surfaces [S. Nie and S. R. Emory, *"Probing Single Molecules and Single Nanoparticles by Surface-Enhanced Raman Scattering"*, Science, 275, 1102-1106 (1997)]. This signal enhancement results from a local amplification of the electric field in the immediate vicinity of metallic objects that permits a significant improvement in the Raman scattering cross section. These gains on the Raman signal are generally referred to as "Surface-Enhanced Raman Spectroscopy" (SERS) or "Surface-Enhanced Resonance Raman Spectroscopy" (SERRS). There are a large number of SERS or SERRS probes prepared using metallic particles or metallic surfaces linked chemically or physically with one or more dye molecules. These probes linked to resonant molecules and the possible signal enhancement with these probes can reach $\sim 10^{14}$. These probes are, however, difficult to prepare, are often toxic (for in-vivo applications) and require preparations or syntheses that are expensive and difficult to reproduce. Moreover, it is difficult to extend these effects to probes or tags having nanometric dimensions.

It has also been observed that the Raman scattering cross section of carbon nanotubes is exceptional, on the order of $\sigma_R \sim 10^{-21}$ cm$^2$ [A. Jorio et al. "Structural (n, m) Determination of Isolated Single-Wall Carbon Nanotubes by Resonant Raman Scattering", Phys. Rev. Lett., Vol. 86, No. 6, 1118-1121 (2001); J. E. Bohn et al. 25 "Estimating the Raman cross sections of single carbon nanotubes", ACS Nano 4 (6), 3466-3470 (2010)]. This property is quasi-unique in the world of nanostructures and is comparable to the resonant Raman cross sections of an aggregate of molecules assembled by stacking in a large structure. The physics of the Raman scattering phenomenon in nanotubes is fairly well understood, because it relates to a resonant process and the object is made up of a number of well-organized atoms (i.e., the nanotube is large relative to a molecule). The nanotube is therefore, in itself, a very interesting Raman probe but, in practice, nanotubes tend to be provided as a mix of different nanotubes, and it is difficult to obtain a sample of nanotubes of the same type. To be useful as a probe, it is necessary to sort the nanotubes by chirality or different isotope composition. [Z. Liu, S. Tabakman, S. Sherlock, X. Li, Z. Chen, K. Jiang, S. Fan, and H. Dai, Multiplexed Five-Color Molecular Imaging of Cancer Cells and Tumor Tissues with Carbon Nanotube Raman Tags in the Near-Infrared Nano Res 3: 222-233(2010)] Only two isotopes of carbon (C12 and C13) are available, which imposes an important limitation to the diversity of the library. Although methods exist for separating nanotubes, they are expensive and produce a very small amount of material. Moreover, a chemical functionalization of a nanotube generally diminishes its Raman signal.

The development of a Raman probe based on carbon nanotubes is interesting, but it remains difficult to use its Raman signal for a clear identification of the probe.

Highly Raman-Active Molecules

Even if the Raman scattering is inefficient, there exists a large number of molecules that are Raman-active. To obtain a strong signal, a high concentration of molecules is necessary in the analysis zone. Despite this limitation, Raman spectroscopy allows the characterization of molecules present in a particular environment. A large set of molecular dyes are strongly active in Raman and this is possible because of their resonance in the visible spectrum. Well known examples include conjugated molecules such as β-carotene, pyridine and rhodamine 6-G. The scattering in these molecules involves resonant Raman and the cross section (by molecule) can attain up to $10^{-24}$ to $10^{-25}$ cm$^2$, at the wavelength of the resonance. [S. Shim, C. M. Stuart, and R. A. Mathies, *Resonance Raman Cross-Sections and Vibronic Analysis of Rhodamine 6G from Broadband Stimulated Raman Spectroscopy*, ChemPhysChem 9, 697-69 (2008)] Despite this, the cross sections are still weak with regard to that which would be necessary for molecular marking or tagging applications. In such a case, it would not be possible to detect a single molecule with resonant Raman, and multiple molecules are necessary in the analysis zone to obtain an acceptable signal. In addition, most of these molecules are unstable under the influence of a high laser intensity and present a luminescence that can diminish or mask a Raman signal.

There is therefore a need for new probes appropriate for optical imaging or molecular marking that have a high sensitivity and can be obtained by relative simple and low-cost preparation methods.

There is a need for new probes appropriate for optical imaging or molecular marking that use Raman scattering, that have a diminished fluorescence and that allow a strong and distinct Raman signal.

There is a need for new probes appropriate for optical imaging and molecular marking and for which a high concentration of probes is not necessary to obtain an acceptable signal.

There is a need for new probes appropriate for optical imaging or molecular marking and based on Raman scattering that are individually detectable and identifiable.

There is a need for new probes appropriate for optical imaging and molecular marking and based on Raman scattering that allow multiple, different dyes to be used simultaneously while each maintaining its specific wavelength signature.

SUMMARY OF THE INVENTION

In accordance with the present invention a Raman scattering probe is provided that includes a capsule of nanometric size to which is coupled a Raman-active molecule that exhibits a Raman scattering response when the probe is illuminated by an excitation light beam. The probe also includes a functionalization chemical group that is attached to an exterior of the capsule and that enables a connection between the capsule and a target material.

In a first embodiment of the invention, the capsule has a shape of a nanotube although other capsule shapes may also be used, and the probe may make use of multiple capsules (e.g., nanotubes) bundled together. The Raman-active molecule may be encapsulated within the capsule or, in an alternative embodiment, may be attached to an external surface thereof or to the functionalization chemical group that is attached to the capsule. It is also possible to have multiple Raman-active molecules coupled to the capsule, and these may be both within the capsule and attached to the capsule exterior. These Raman-active molecular assemblies may be different from one another such that each contributes a different Raman scattering response when the probe is illuminated by an appropriate excitation light beam.

A variety of different functionalization chemical groups may be used with the probe. In one embodiment, the functionalization chemical group bonds directly with the target material. The functionalization chemical group may be specific to one or more target materials. The functionalization chemical group may be a dispersive chemical group that facilitates the dispersion or solubility of the probe in a liquid medium containing the target material, such that a plurality of probes introduced in the fluid environment will remain dispersed therein. In yet another embodiment, the functionalization chemical group may have a generic chemical functionalization that bonds with any of a plurality of secondary chemical groups each of which, in turn, is capable of bonding with the target material. The probe may also be functionalized by different functionalization chemical groups simultaneously. The different types of functionalizations may also be combined with the same probe, such that multiple functionalization chemical groups are attached to the same capsule. This may enable the same probe to bond with multiple target materials, such as a plurality of target molecules of the same type or of different types, or with one or more target molecules while also with a solvent that promotes dispersion of the probes in a fluid.

The present invention also includes a method of preparing a Raman scattering probe as described above. The method includes providing a capsule of nanometric size such as a nanotube. If not previously prepared, the method may also include a first step of cleaning and opening of the unprocessed nanometric capsule. A Raman-active molecule is then coupled to the capsule, being either encapsulated within the capsule or attached to an exterior of the capsule. Attachment to the capsule exterior may be either by attachment directly to an external surface of the capsule or by attachment to a functionalization chemical group attached to the capsule external surface. Preparation of the capsule also includes attachment of a desired functionalization chemical group to the capsule external surface. The attached functionalization chemical group may bond directly or selectively to a target material, or it may be a generic functionalization chemical group that bonds with any of a plurality of secondary chemical groups each of which bonds directly with a different predetermined target material. The functionalization step may precede or follow the introduction of the Raman-active molecule.

In another aspect of the invention, a probe as described herein may be used for performing a Raman investigation of a sample. In particular, a Raman probe as described above is attached to a target material of interest within the sample, the Raman scattering probe comprising a capsule of nanometric size to which is coupled at least one Raman-active molecule. The probe is attached to the target material via at least one functionalization chemical group that is attached to an exterior of the capsule and that forms a bond with the target material. The method further includes illuminating the sample with an excitation light beam having a wavelength that causes a Raman scattering response in the Raman-active molecule, and detecting light resulting from the Raman scattering response, using an appropriate detector. The investigation may be a Raman imaging or Raman spectroscopic application.

The invention and its advantages will become more apparent from the detailed description and examples that follow, which describe the various embodiments of the invention.

BRIEF DESCRIPTION OF THE DRAWINGS

FIG. 3A is a schematic view of the encapsulation of 6T in a nanotube indicating schematically that the capsule is large compared to the molecules.

FIG. 3B is a graphical view of the absorption spectrum of α-sexithiophene (6T) encapsulated in a single-wall carbon nanotube (6T@SWNT) in dimethylformamide (DMF).

FIG. 12A shows a diagram of the insertion reaction of toluidine blue by external attachment to nanotubes (where "CNT" represents the carbon nanotubes, and "DMF (anhydre)" refers to the anhydrous DMF).

FIGS. 16A and 16B are SEM and Raman intensity mapping images, respectively, of 6T@SWNT probes deposited and patterned as a cross on an oxidized silicon substrate. FIG. 16C is an overlapped composite of FIGS. 16A and 16B.

DETAILED DESCRIPTION

Figure 1A:
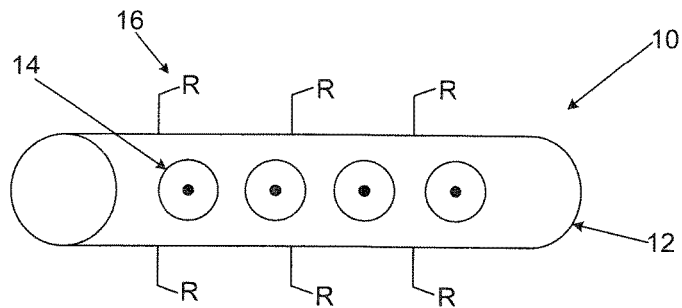
FIGS. 1A, 1B and 1C are schematic views of Raman scattering probes according to three illustrative embodiments of the invention.

In accordance with an aspect of the invention, probes are provided for use in Raman scattering spectroscopy. The probes according to this aspect of the invention each include a capsule of nanometric size, at least one Raman-active molecule that is inserted in the capsule or attached to its external surface, and at least one functionalization chemical group attached to the exterior of the capsule.

The term "capsule" as used herein refers to the basic structure forming the probe according to the invention. The capsule is the basic structure to which is associated the Raman-active molecule.

This basic structure or capsule is also functionalized along its outside surface by one or more chemical groups. The capsule can be any container of a nanometric size having a spherical, cylindrical, conical or other shape known to those skilled in the art. For example, the container can be a carbon nanotube (single wall, double wall or multiwall), a boron nitride nanotube or a fullerene (C60, C70, etc.).

The expression "nanometric" refers to the size of the capsule defined above along at least one orientation. In some embodiments, this expression refers to the diameter of the structure having a spherical, cylindrical, conical or other hollow shape forming the capsule. This diameter is, in general, on the order of 0.3 nm to 5 nm. The length of the capsule may vary, according to the application, from 1 nm to 1 mm, and is therefore not limited to nanometric dimensions.

The terms "bond", "bind", "attach", "connect" or "couple" refer to a chemical, an electrostatic or a physical connection between the capsule and the molecules being either the Raman-active molecule or the functionalization chemical group.

The terms "Raman-active molecules", "molecules active for Raman scattering", "dye molecules", and "dyes" are used independently to define the active molecules that are encapsulated in the capsule used for forming the probe or attached to the exterior thereof. The Raman-active molecule exhibits a Raman scattering response when the probe is illuminated by an excitation light beam of an appropriate wavelength, that is, it is detectable and identifiable by Raman spectroscopy. A strong Raman signal is also possible if the molecule offers an optical resonance in the range of laser excitation wavelengths available with the Raman apparatus that is used. A large variety of active molecules is therefore anticipated and those skilled in the art of the invention will be able to identify the appropriate molecule to use. For example, active molecules can be derivatives of oligothiophenes, carotenoids (such as β-carotene), methylene violet B having the formula:

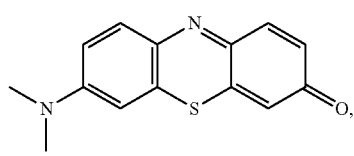 [SMILES: CN(C)c1ccc2nc3ccc(=O)cc-3sc2c1]

Toluidine Blue, "Fast Black K salt (FBK)", and DTDCI having the formula:

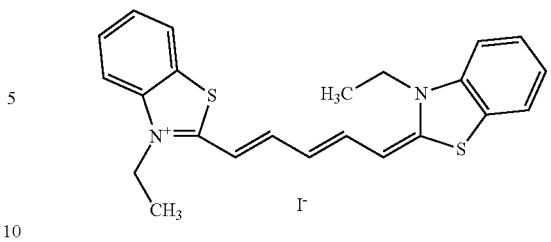

Oligothiophene derivatives are, for example, derivatives of 3,6-dithiophen-2-yl-2,5-dihydro-pyrrolo[3,4-c]pyrrole-1,4-dione (DPP derivatives). To this is added all the Raman resonant molecules in the visible spectrum such as chromophores or oligomers based on a π-type conjugation. Some notable examples include the oligomers of conjugated polymers such as carbazoles, polyaniline, polyfurans, polyfluorene, polypyrroles, paraphenylenes or polyheteroatomic vinyls, etc. There are also large polyaromatic molecules such as fullerenes, pentacene derivatives, anthracene, perylene, porphyrin, naphthalene, etc. and the well-known systems in resonant Raman such as benzotriazoles (e.g., 6-tolyltriazole), rhodamines (e.g., rhodamine 6G), pyrolines (e.g. pyroline G and thiopyronine). The use of isotope derivatives of these Raman-active molecules widens the choice of molecules that will give different Raman signatures.

For the purposes of the present disclosure, the term "Raman" refers to the physical phenomena of "inelastic scattering" of monochromatic light, usually from a laser source. Interaction of a photon from the source with matter, such as a molecule in a sample material, results in a photon having a different energy, and therefore a different wavelength. This energy difference corresponds to a vibrational state of the molecule and can result in an energy gain or loss to the photon, depending on the original vibrational state of the molecule. A loss of energy to the molecule causes a shift to a longer wavelength (referred to as a "Stokes" shift), while a gain of energy from the molecule causes a shift to a shorter wavelength (referred to as an "anti-Stokes" shift). Raman scattering from a given molecule will produce a Stokes or anti-Stokes wavelength shift having a particular energy, and this wavelength shift may be detected and used to identify molecules present the sample material. "Raman spectroscopy" refers to the spectral analysis of light scattered at a particular location, whereas "Raman imaging" refers to the detection of photons resulting from Raman scattering at a plurality of points in a two- or three-dimensional field that may be used to form an image indicative of the relative location of Raman-active materials within the field. One skilled in the art will readily understand that the expression "Raman investigation" can refer to Raman spectroscopy, Raman imaging or any other technique which involves relying on Raman scattering to obtain information from a molecule or system.

The expression "functionalization chemical group" or "chemical group" refers to groups attached to the exterior of the capsule. The chemical groups can be either attached directly to the external surface of the capsule or attached to the Raman-active molecule when it is attached to the exterior of the capsule. The chemical groups are groups that facilitate the dispersion or the solubility of the probe in a liquid medium, or that allow the probe to be compatible with the medium and/or permit the selective adhesion of the probe to specific molecular sites. For this, a great number of different strategies can be adapted to the different anticipated applications. For example, the addition of positive or negative charges on the capsule from chemical groups such as carboxylic acids or amines allow a selective association with a substrate with an opposite charge. The use of a DNA or RNA group in association with its complement or of a protein with its receptor are other good examples for developing applications for molecular marking for medical diagnosis or screening.

The expression "target material" refers to any molecule, group of molecules, cell, solvent, or the like to which a functionalization chemical group may be attached. It will be understood that, depending on the nature of the target material, the functionalization group may attach itself to the entire target material or to a portion thereof.

Description of Probes According to Illustrative Embodiments of the Invention

Figure 1B:
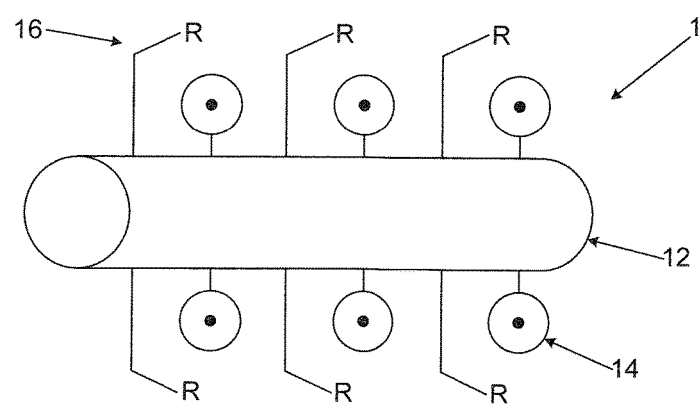
Figure 1C:
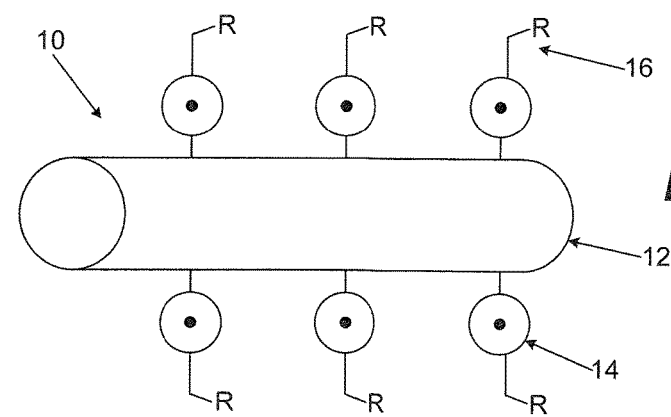

FIGS. 1A, 1B and 1C represent probes according to a possible embodiment of the invention. Probe 10 has a base structure embodied by capsule 12. This capsule plays an important structural role in the probe, but it could also serve as a spectroscopic reference when processing the Raman spectrum of the probe.

The capsule 12 shown in FIGS. 1A, 1B and 1C has a cylindrical shape. For example, a capsule with a cylindrical form could be a carbon nanotube or a boron nitride nanotube (BN nanotube). The capsule may also be a small bundle or aggregate of few nanotubes. It is noted that the capsule 12 could also have a spherical shape such as, for example, a fullerene (C60, C70, etc.) or a conical shape such as, for example, a nanohorn, or any other shape known to those skilled in the art. In the case of a nanotube, the capsule can be a single wall, double wall or multiwall nanotube. The capsule 12 has a nanometric size and, more specifically, the diameter of the capsule is, in general, on the order of 0.3 nm to 5 nm. For a nanotube capsule, its length is, in general, on the order of 0.5 nm to 1 mm.

The probe 10 also includes at least one Raman-active molecule 14. As can be seen in FIGS. 1A, 1B and 1C, the probe can include more than one Raman-active molecule 14, which can be either identical or different from one another.

As shown in FIG. 1A, the active molecules 14 are inserted (encapsulated) in the interior of the capsule. This requires that any such active molecule has a dimension that permits the molecule to be properly inserted in the capsule and maintained in the interior by non-specific van der Waals or electrostatic interactions. Alternatively, as shown in FIGS. 1B and 1C, an active molecule can be attached chemically, electrostatically or physically to the external surface of the capsule 12. Those skilled in the art will understand that, for a given capsule, it is also possible to encapsulate an active molecule in its interior while attaching an active molecule of the same or of a different type to its external surface.

The active molecules 14, also referred to as "dye molecules" or simply "dyes," are molecules that are active in Raman scattering, that is, which can be detected and identified by Raman spectroscopy. This is possible if these molecules offer an optical resonance in Raman in the wavelength range of an excitation laser of the Raman apparatus that is used. A large variety of active molecules is therefore anticipated and one skilled in the art will be able to identify which molecules to use. For example, the active molecules can be derivatives of the type oligothiophenes, of carotenoid such as, for example, β-carotenes, methylene violet B having the formula:

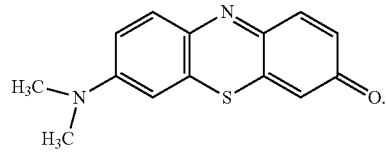

Toluidine Blue, "Fast Black K salt (FBK)", and DTDCI having the formula:

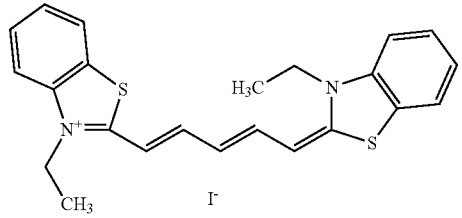 [SMILES: CCN1\C(=C/C=C/C=C/c2sc3ccccc3[n+]2CC)Sc2ccccc21 ; [I-]]

The oligothiophene type derivatives are, for example, DPP (3,6-dithiophen-2-yl-2,5-dihydro-pyrrolo[3,4-c]pyrrole-1,4-dione) or the DPP derivatives. DPP derivatives could be, for example, DPP(2), having the following formula:

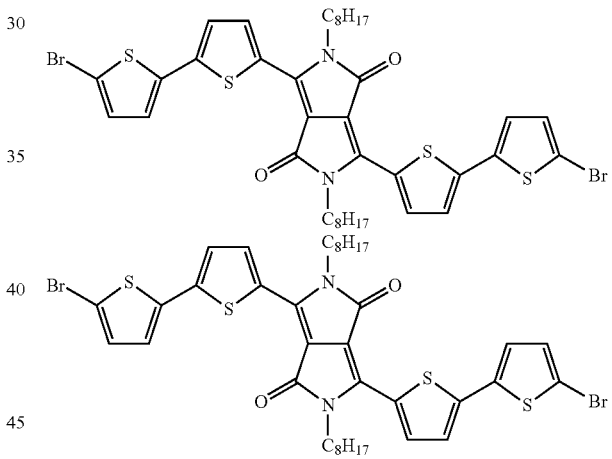

DPP(2)Br$_2$, having the following formula:

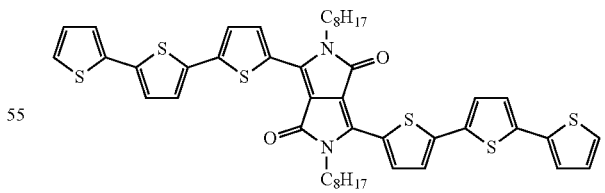

or DPP(3), having the following formula:

To this is added the Raman-active molecules such as chromophores or oligomers based on a π-type conjugation. For example, there are notably oligomers of conjugated polymers such as carbazoles, polyaniline, polyfuranes, polyfluorene, polypyrroles, paraphenylen or polyhetero-atomic vinylens. There are also large polyaromatic molecules such as fullerenes, derivatives of pentacene, anthracene, peryleneporphyrin, or naphthalene, etc. and systems well known in Raman resonance such as benzotriazoles (e.g., 6-tolytriazole), rhodamines (e.g., rhodamine 6G), pyrolines (e.g., pyroline G and thiopyronine), etc. The use of isotope derivatives of these Raman-active molecules widens the choice of molecules that will give different Raman signatures.

It is noted that the probe 10 can include multiple active molecules that are identical or multiple active molecules that are different, each having its own Raman resonance. The interest with these more complex probes is to permit a Raman detection of probes using different wavelengths.

The probe 10 shown in FIGS. 1A, 1B and 1C is also functionalized by chemical groups 16 attached to the exterior of the capsule 12. In FIGS. 1A and 1B, the chemical groups 16 are attached directly to the surface of the capsule while, in FIG. 1C, the chemical groups are chemically linked to active molecules that are themselves attached directly to the external capsule surface.

The chemical groups 16 can be of different varieties.

According to their nature, the groups may also permit a selective adhesion of the probe at specific molecular sites of the target material. The chemical group may be specific to a given target material, or multi-specific, that is that is can attach to any one of a plurality of target materials. Those skilled in the art will understand how to select the appropriate chemical groups according to the recommended use of the probe. There exist many different functionalization strategies depending on the intended application. For example, the addition of positive or negative charges to the capsule with the groups such as carboxylic acids or amines permits a selective association with an oppositely charged substrate.

The notable usage of a DNA or RNA group for an association with its complement or of a protein with its receptor are other good examples for medical diagnosis, tagging and scanning applications. According to an embodiment of the invention, the chemical group can be a halogenophenyl group, such as iodophenyl or bromophenyl. These groups can themselves be easily functionalized to form other chemical groups.

In another example the functionalization chemical group may be a dispersion chemical group which facilitate the dispersion of solubility of the probe in a liquid material. For example, a lipid membrane medium requires the addition of aliphatic hydrophobic groups while aqueous media require instead polar or charged groups.

In yet another example the functionalization chemical group can be a generic group which can bond with any of a plurality of secondary chemical groups, which themselves can attach to the target material. The probe may be provided with only the generic functionalization for subsequent specific functionalization, or already provided with both the generic and secondary functionalization groups.

It will be readily understood that a given probe may combine a variety of different types of chemical groups, such as dispersion, generic, specific or multi-specific to one or several target materials.

The Raman scattering probes according to some embodiments of the invention present numerous advantages such as, for example:

i) The capsule can protect the active molecules encapsulated therewithin. For example, carbon nanotubes do not oxidize in normal conditions and are very resistant to different chemical and thermal treatments. This protection also permits Raman-active molecules to resist extreme conditions of heat or chemical corrosion.

ii) By being isolated in the capsule, strong interactions can be prevented between the active molecules and the medium in which the probes are dispersed. Alternatively, and according to the desired application of the probe, such interactions can be encouraged when the active molecules are on the capsule exterior.

iii) Due to the chemical functionalization (covalent or non-covalent) of the capsule, the probes can offer very specific chemical affinities. The probes are thus compatible with a variety of media and can be adapted to specific applications such as molecular marking.

iv) The nanometric dimension of the probe as well as the numerous functionalizing possibilities provide a great versatility to better target a particular application. For example, it can offer the possibility of including chemical groups that act as recognition sites for one or more specific substrates.

v) For such a probe, it is possible to attach multiple different functions to the surface of the capsule, thus making different applications possible for the same probe.

vi) Embodiments of the probes offer little or no parasitic emission (fluorescence or phosphorescence of the molecules) superimposed on the Raman signal. The Raman optical signal to noise ratio is therefore improved.

vii) Each probe possesses a unique Raman signature and multiple probes can be differentiated from one another by comparison of their Raman spectra.

viii) The probes can be optimized for one specific excitation wavelength in choosing active molecules that are in resonance with the excitation light beam.

ix) Each probe presents an exceptional sensitivity for Raman detection and it is possible to obtain a strong signal permitting identification of an individual probe. In Raman imaging, it is therefore possible to identify the presence or absence of a probe at a precise location with a high spatial resolution of 500 nm or less.

x) Some probes may be composed of one or more active molecules oriented with regard to the capsule, which confers an anisotropy in the Raman signal with regard to the polarization of the excitation light. This anisotropy therefore allows the measurement of orientation of the probe in the medium.

xi) In some embodiments, residues of probe fluorescence combine with the Raman signature (at a wavelength where there is little fluorescence), allowing a more sensitive and specific detection of the probes. It is thus possible to have a coupled usage of capsule type probes in fluorescence and Raman.

As indicated below, the Raman scattering probe according to embodiments of the invention can have a wide range of applications, including molecular marking in spectroscopy and Raman imaging. In a general context, a Raman scattering probe as described above may be functionalized for a particular target molecule, using either a functionalization chemical group that bonds directly with the target molecule, or a generic chemical functionalization that bonds any of a number of secondary chemical groups each of which bonds directly with a different target molecule. When applied to a sample material, the probe is attached to a target molecule or a site of interest within the sample. The sample is then illuminated with an excitation light beam having a wavelength that causes a Raman scattering response in the Raman-active molecule. Light from the Raman scattering response is then detected and is indicative of the presence of the target molecule. An imaging apparatus may also be used to detect the light from the Raman scattering response at a plurality of points across a surface of the sample, thus allowing the formation of an image indicative of the relative location of the target molecules.

Some examples of how the probes may be used include medical applications for which the probes functionalized by appropriate chemical groups can be, for example, used to identify the presence or absence of a membranous receptor on a cell or a protein in the blood. In vitro, the probes can be applied to identify a pathogen or an unhealthy cell. When specific to a receptor, they can be inserted in a living being and serve as a tool for establishing a medical diagnosis or for localizing the presence of unhealthy or cancerous cells. Moreover, these probes can be used as contrast agents in biomedical Raman imaging.

In other specific applications such as, for example, in the area of civil security and/or forensics, the probes can be used for detecting trace compounds such as explosives, drugs, DNA, RNA, proteins or hormones. These Raman probes can also be used in the identification of documents. The insertion of a specific probe in the material of the document and the identification of it by Raman analysis of the document offers rapid means of obtaining solid proof of the authenticity of a document.

As a research tool, the probes according to the invention can serve as optical tracers for studying complex processes such as metabolism and physio-chemical, biochemical and biological systems. The notable use of probes in a microfluidic system allows the localization by Raman measurement of the presence or absence of a substance or a cell in one of the channels of the device. This identification can be used for further tasks such as sorting, derivation or labelling the substance or the cells.

Description of Preparation Methods According to Embodiments of the Invention

In accordance with another aspect of the invention, there is also provided a method of preparing a Raman scattering probe.

Figure 2:
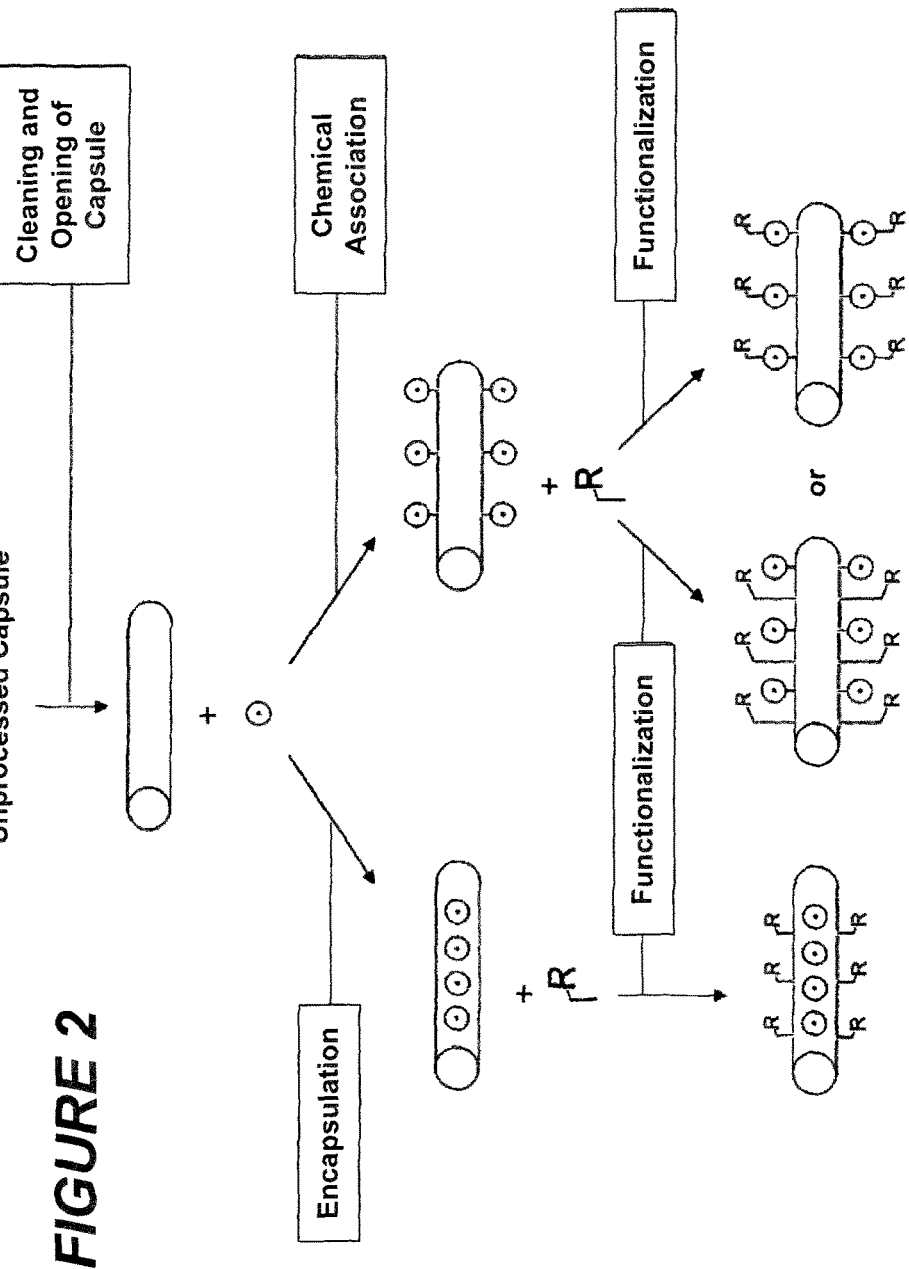
FIG. 2 is a schematic view of the different process steps for preparing Raman scattering probes according to an illustrative embodiment of the invention.

FIG. 2 shows the different steps for the method of preparing a Raman scattering probe as described above. The method includes a first step of providing a capsule of nanometric size. Optionally, the method may involve cleaning and opening the unprocessed nanometric capsule. According to an illustrative embodiment, this step may involve a cleaning of the capsules by reflux in concentrated nitric acid. The treatment in nitric acid allows both the cleaning and the opening of the capsules to enable the subsequent encapsulation. After the cleaning and opening of the capsules, it is desirable to filter them with a porous membrane using a vacuum pump and to air-dry them. The capsules thus dried are removed from the filter and can thereafter be placed in deionized water for subsequent hydrothermic treatment. At the time of this treatment, the capsules are functionalized by oxidized groups such as —COOH, —OH and =O. The hydrothermic treatment occurs generally under reflux and constant agitation in a period of about three hours. The aqueous phase is thereafter eliminated by filtration. The capsules are then cleaned using a solvent and dried in a vacuum. An example of this detailed procedure is presented below for the cleaning and opening of carbon nanotubes. The capsules may also be shortened by cutting them using an ultrasonic treatment in a liquid or in an acid solution, and sorted by size or by material properties (such as whether metallic or semiconductor) using chromatography or ultracentrifugation in a density gradient.

In a second step as shown in FIG. 2, one or more Raman-active molecules are coupled to the capsule. In some embodiments, this coupling may be accomplished by either insertion in the capsule (encapsulation) or linked by a chemical bond to the external surface of the capsule, thereby forming a capsule-active molecule composite. It is also possible that active molecules are both encapsulated in the capsule and attached to its external surface.

Encapsulation can be done in vapour phase or liquid phase. In one embodiment, the gaseous method is preferably done in a container, such as an ampoule, under vacuum. The container is filled with the clean and opened capsules and with a supply of molecules to encapsulate. A simple heating of the container to the sublimation temperature of the molecules to be encapsulated induces the encapsulation. A complete encapsulation takes generally several hours. The non-encapsulated molecules are then removed using solvents or by sublimation of the free molecules. The method of liquid phase encapsulation involves dispersing the open capsules in a solvent containing the molecules to be encapsulated dissolved therein to saturation. A reduction of the solubility of the molecules to be encapsulated in the solvent is thereafter carried out by slow reduction of the temperature, by slow evaporation of the solvent or by the slow replacement of the solvent by another solvent that is less favorable to the solubility of the active molecules. The encapsulation in liquid or vapour phase is a spontaneous thermodynamic process.

In other embodiments, the chemical association of the active molecule on the external surface of the capsule can be done with a carbon-carbon coupling reaction using a free radical reaction of the molecule with the capsule. More details on this type of reaction are given below such as, for example, in the case of a carbon nanotube probe having attached to its external surface an active molecule of toluidine blue.

In a third process step for preparing the probes according to the present invention, at least one functionalization chemical group is attached to an external surface of the capsule. This functionalization makes the probe compatible with a liquid or aqueous medium or a receptor or both. For this, a functional group R is attached directly to the capsule or attached to an active molecule that is attached to the exterior of the capsule. The functionalization by the functional group is, in general, accomplished by covalent bonding in an aqueous medium or in a solvent with free radical reagents. An example of a free radical reagent is a phenyldiazonium salt or a derivative of the diazonium salt. The invention is not limited to these reagents and one skilled in the art will know how to choose other types of reagents providing addition reaction to the capsule. The excess of reagents are subsequently eliminated using, for example, a solvent and filtration with a PTFE membrane. Subsequent reactions with the groups enable different varieties of functionalization. The choice of chemical group depends on the particular application intended for the probe. Details of some reactions possible with carbon nanotubes are presented below. General information is also available in recent literature on chemical attachment to carbon nanotubes.

Functionalization by a chemical group R attached to the capsule can be either a "generic" functionalization or a "target-specific" functionalization. A target-specific functionalization involves a chemical group that is both attached to the capsule and that attaches directly to a target molecule of interest, that is, a molecule that is to be tagged by the probe. While the target-specific functionalization allows the direct bonding between the probe and the target, it requires that the probes be developed individually for each marking application. In another embodiment of the invention, a probe may instead be formed with a "generic" functionalization that may be subsequently modified to render it specific to a particular target.

The concept of a generic functionalization is known in the art with regard to other types of molecular markers. In such a case, the functionalization provided with the probe is not one that is target specific but, rather, one that may be easily linked to another chemical group that is target specific. Thus, referring again to FIGS. 1 and 2, the chemical group R, if generic, would have a chemical structure that allowed the easy attachment of a wide variety of possible secondary chemical groups that, in turn, were target-specific. Thus, the generic functionalization and the additional chemical group would together function as the link between the capsule and the target molecule. In this way, probes with a generic functionalization can be produced in large quantities and subsequently tailored to a specific application.

One example of a generic functionalization makes use of the compound polyethylene glycol (PEG). Variants of this compound may be used to attach to the external surface of the capsule, and have a chemical structure that bonds easily with other chemical groups. Thus, a probe produced with a PEG-based functionalization may be modified by a user to attach a desired target-specific chemical group and thereby render the probe target-specific.

Finally, a non-covalent functionalization with surfactants or polymers such as pluronic or PEG can also be implemented so as to better stabilize the probes in the aqueous medium. In this case, slight oxidation of the capsule at the time of the cleaning step is useful for stabilizing the surfactant-capsule composite. This step involves the addition of a surfactant (or a polymer) to the solution of probes and a subsequent activation of the mixture by an ultrasound treatment. A final step of centrifugation serves to keep the probes in solution for extraction of the largest aggregates. This procedure is used for dispersing the carbon nanotubes.

According to another embodiment of the method for obtaining the probes according to the present invention, the third step described above is implemented before the second step. In effect, it is possible to functionalize the capsule by the chemical group R before forming the capsule-active molecule composite.

It is possible to develop a very large variety of different Raman probes using the method described above. The number is almost infinite and depends on the application and the wavelengths anticipated and available for use with the Raman instrument.

Examples of Encapsulated Raman Probes and their Methods of Fabrication

In the following examples, Raman scattering probes according to the invention were prepared using single wall carbon nanotubes each having a diameter of ~1.4 nm and lengths between 100 nm and 5 μm or more. The chemical group attached to the surface of the nanotube is bromophenyl or phenyldiazonium group. Different active molecules were encapsulated in the SWNT, such as is described in detail below. Another type of probe was also prepared using double wall carbon nanotubes (DWNT). In this case, toluidine blue is used as an active molecule and is fixed by covalent bond to the external surface of the nanotube.

The inventors have determined that individual SWNT probes chemically functionalized with dyes show exceptional Raman scattering properties. Depending on the position of the dye, external or internal to the carbon nanotube, a general protocol of synthesis in three steps is used: i) opening and cleaning of the nanotubes; ii) encapsulation of the dye; and iii) covalent reaction on the external layer. The details concerning the step of encapsulation are specific to the dye used, but steps i) and iii) are the same for all the probes.

i) Protocol of Opening and Cleaning of the Nanotubes

All of the nanotube samples were washed beforehand by reflux in concentrated nitric acid. This protocol allows the cleaning of the nanotubes, the functionalization with —COOH groups and the opening of ends of the nanotubes to allow the encapsulation. The procedure used is as follows: a mass of 100 mg of unprocessed SWNT is placed in 300 ml of 67% nitric acid (Fisher). The mixture is heated to reflux under constant agitation for a period of four hours. The nanotubes are then filtered with a 1.22 μm PTFE membrane using a vacuum pump. The resulting film, generally referred to as "buckypaper", is air-dried. It is subsequently removed from the membrane and placed in 300 ml of deionized water (18.2 MΩ—Millipore) to undergo a hydrothermic treatment. As with the acid treatment, this treatment proceeds under reflux and constant agitation for a period of three hours. The aqueous phase is eliminated by filtering with a 1.22 μm PTFE membrane. The "buckypaper" is finally washed with a solvent and dried under vacuum until it may be easily removed from the membrane. Generally, the final mass of carbon nanotubes is between 40 mg and 60 mg.

iii) Protocol of Covalent Functionalization of the External Surface of the Carbon Nanotubes with a Chemical Group R The reaction of functionalization is implemented in an aqueous medium having a weak concentration of phenyldiazonium. A deoxygenated solution of tetrafluoroborate 4-bromophenyl diazonium 0.79 mM (96%, Sigma-Aldrich) at a pH ~10 is first prepared. The adjustment of the pH is realized by an addition of sodium hydroxide. The encapsulated SWNT are then immersed in a solution for ten minutes under agitation at room temperature, and are finally rinsed with deionized water and diethylether.

Multiple variants of these functionalizations (i.e., using different chemical groups R) are possible so as to adapt the capsule probes for one application or another. For example, an attachment of toluidine blue, a Raman-active molecule, to the exterior of the capsule is possible using a covalent reaction on the group R remaining from the step of functionalization by diazonium salt (preceding step). Another example demonstrated by the inventors is the attachment of a negatively charged chemical group to the same group R to allow the selective assembly of nanotubes on a surface. The variations of functionalization are practically infinite and depend on the anticipated application.

Example 1: Probes of the Type Oligothiophene@SWNT a) Probes α-sexithiophene@SWNT The assembly of α-sexithiophenes(6T) in carbon nanotubes is known in the prior art. [M. A. Loi, J. Gao, F. Cordella, P. Blondeau, E. Menna, B Bartova, C. Hébert, S. Lazar, G. A. Botton, M. Milko, et C. Ambrosch-Draxl, Adv. Mater. 22, 1-5 (2010)] FIG. 3A illustrates the encapsulation of 6T in the nanotube and shows schematically the large size of the capsule relative to the molecules.

Figure 4:
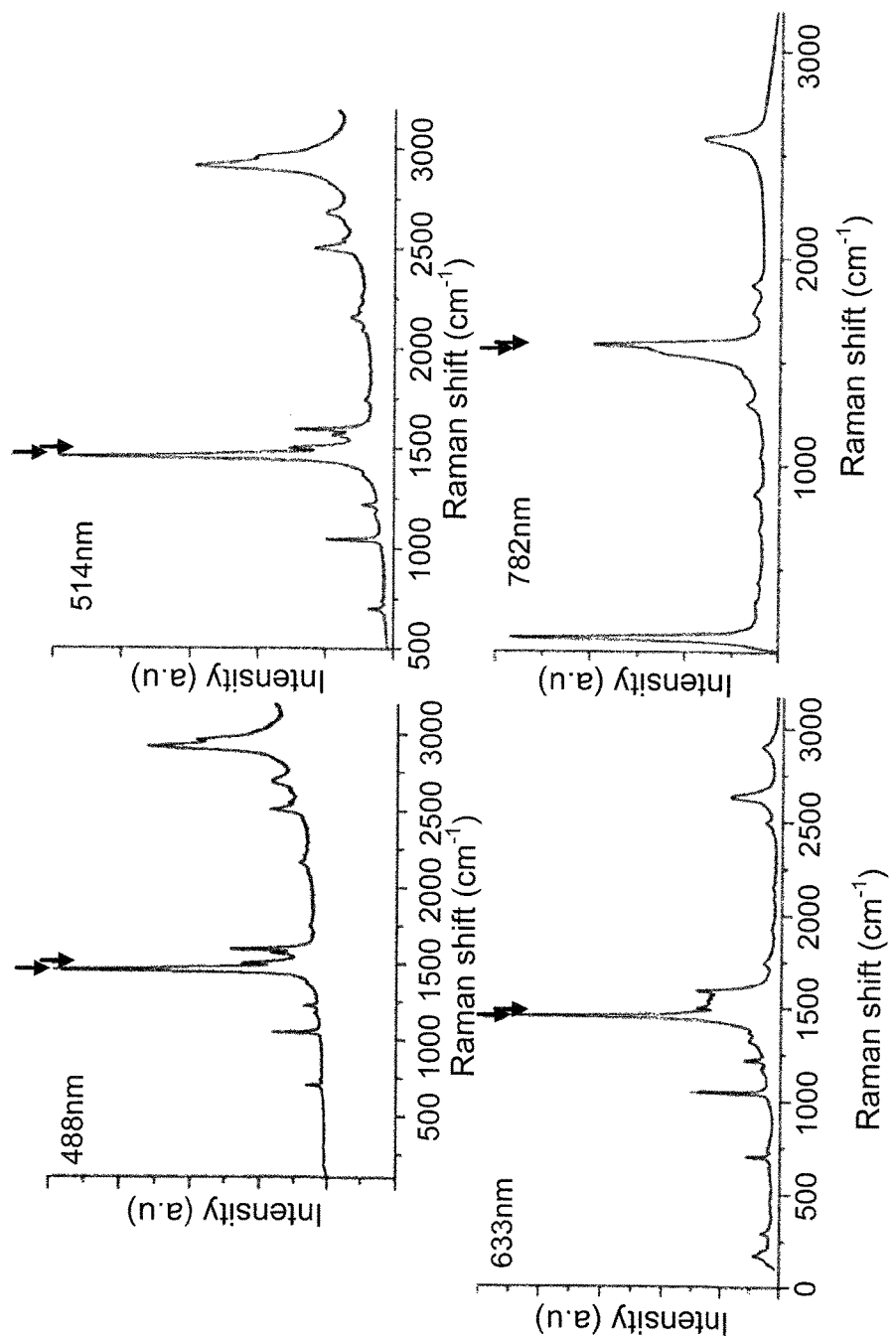
FIG. 4 is a graphical representation of the complete Raman spectra for a powder form of 6T@SWNT for excitation wavelengths of 488 nm, 514 nm, 633 nm and 782 nm, respectively.
Figure 5:
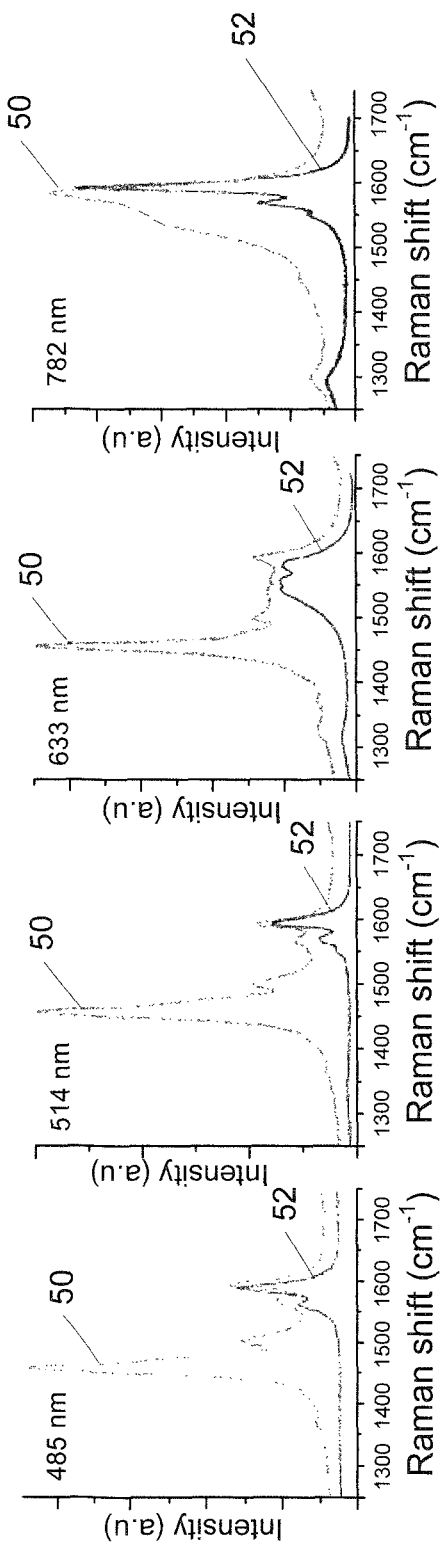
FIG. 5 is a graphical representation of the complete Raman spectra for a powder form of 6T@SWNT compared to the spectra of the single-wall carbon nanotubes (SWNT) alone using excitation wavelengths of 488 nm, 514 nm, 633 nm and 782 nm. The spectrum of 6T@SWNT is shown in the upper spectrum, and the spectrum for pristine nanotube is shown in the lower spectrum.

Measurements of absorption and Raman scattering on the powder form of 6T@SWNT composites, of a solution containing them and on the samples of individual 6T@SWNT composites deposited on a silicon substrate, were done by the inventors. To disperse the 6T@SWNT deposits in a solvent solution, the samples were functionalized by chemical oxidation in concentrated $HNO_3$. This step permits the attachment of COOH functions on the exterior of the nanotubes. The absorption spectrum of the functionalized 6T@SWNT powder, shown in FIG. 3B, has a principal absorption band located at about 510 nm and several other absorption bands between 600 nm and 1200 nm. The band at 510 nm is associated with dye molecules of 6T, while the other bands (900-1200 nm and 600-800 nm) are associated with the optical absorption of carbon nanotubes. The Raman spectra of these signals were measured at different excitation wavelengths (782, 633, 514, and 488 nm, as indicated in FIG. 3B). The individual Raman spectra of the sample powder at each of the excitation wavelengths are presented in FIG. 4. FIG. 5 shows the spectra of FIG. 4 in the region around 1500 cm$^{-1}$ and compares them to the spectra obtained for the unprocessed carbon nanotubes. In this figure, the spectra of the 6T@SWNT composites are indicated by reference numeral 50, while the spectra of the unprocessed carbon nanotubes are indicated by reference numeral 52. The band located around 1457 cm$^{-1}$ in the Raman spectrum is the most distinct signature of the encapsulated α-sexithiophene. A comparison with the spectra of nanotubes without the dye allows an identification of the other less-intense bands associated with the nanotubes. The signal from the dye is more intense than that of the nanotubes when the excitation wavelength is close to, or directly in resonance with, the dye, at either 633 nm, 514 nm or 488 nm. However, at 782 nm, the signal attributable to the 6T is less intense relative to that of the nanotubes. These measurements illustrate the resonant character of the process of Raman scattering with the 6T@SWNT. FIGS. 4 and 5 show that there is a resonant process because the Raman signal of the α-sexithiophene is much more intense only when the wavelength of the excitation energy is near that of the absorption energy of the α-sexithiophene.

The Raman measurements of the 6T@SWNT composite allow observation of a strong Raman signal coming from the molecules and determination that resonance is essential for maximizing Raman scattering. However, a measurement of the powder does not allow a determination of whether the Raman scattering of the molecules is strong or not. In this first experiment, the inventors have nevertheless noticed that there is no fluorescence signal, even beyond the zone of the spectrum presented here. This characteristic makes measurement of the spectrum easy to achieve because there is no fluorescence noise. To determine the strength of the Raman signal, the inventors performed supplemental experiments on the individualized 6T@SWNT. The results presented in FIG. 6 demonstrate that the Raman signal of the molecules at the resonance energy is stronger than that of the nanotubes. This experiment is performed on a small bundle of α-sexithiophene@nanotubes that have a length of approximately one micron and that are positioned on a surface of silicon oxide. The AFM image of the probe is shown at the left in FIG. 6. The local Raman measurement at the position of this probe is shown at the right in FIG. 6. The band associated with the dye and its intensity at 633 nm is clearly visible in the spectrum. The intensity is higher than that of the nanotube. With this measurement, it may be concluded that the Raman signal of the α-sexithiophene molecules is generally stronger than or similar to that of the nanotubes. As the cross section of the nanotubes is $\sigma_R \sim 10^{-22}$ cm$^2$, this measurement demonstrates that the cross section of the molecules in the beam is important. This measurement allowed the inventors to conclude that this type of composite presents outstanding properties and that it is very interesting for obtaining strong Raman signals.

Raman Scattering Cross Section of α-Sexithiophene@SWNT Probes

Figure 6:
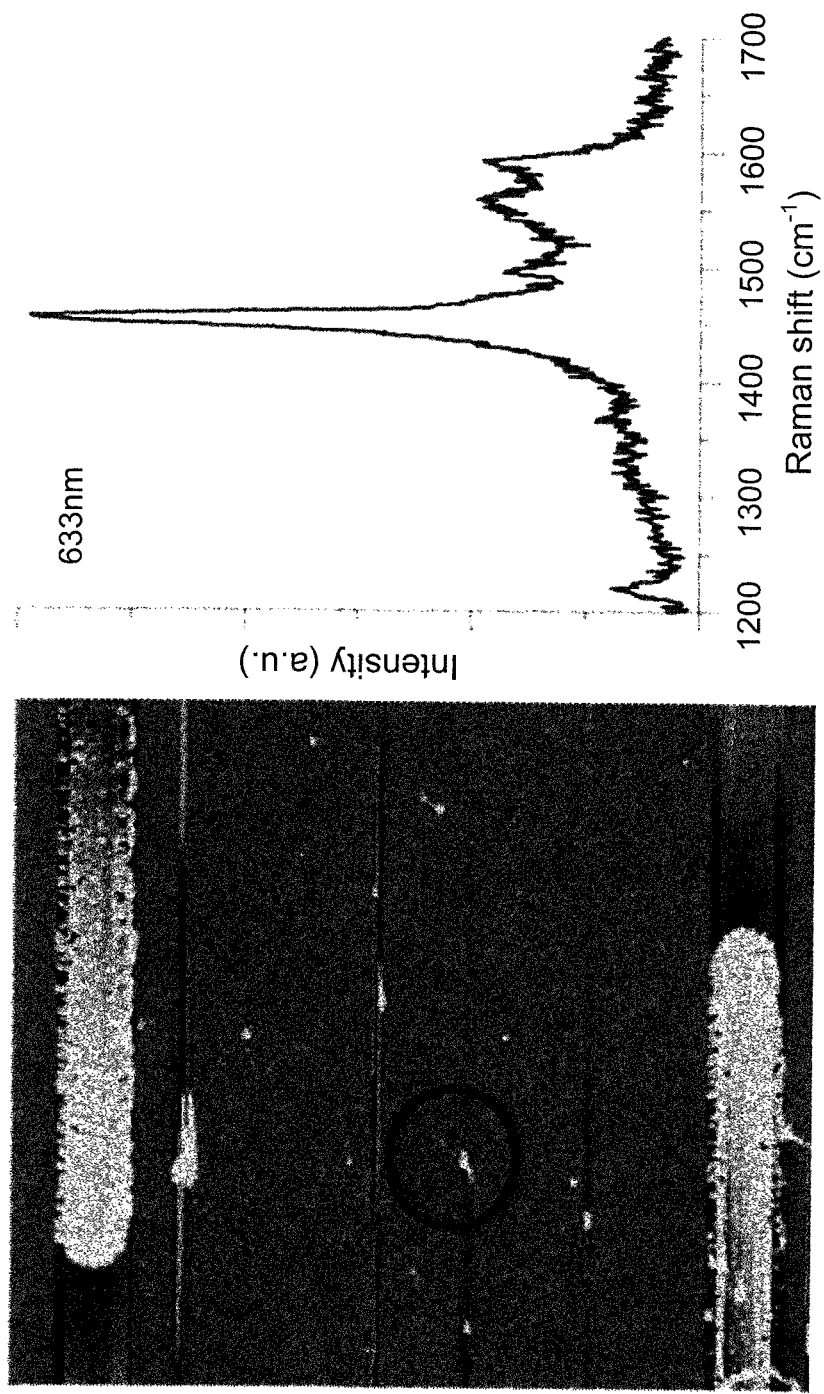
FIG. 6 is an image obtained using atomic force microscopy (AFM) (left side of the figure) of 6T@SWNT deposited on a silicon substrate. The AFM image reveals a bundle of 6T@SWNT of approximately three nanometers in height. This figure also shows the Raman spectrum (right side of the figure) of the small aggregate imaged on the left which is composed of two or three probes localized in the same region. The excitation wavelength is 633 nm.

A first way to estimate the cross section of the Raman scattering of molecules in FIG. 6 is to use the Raman scattering of the nanotubes as an internal reference. It is believed that the scattering cross section of the nanotubes is in the range between $3 \times 10^{-23}$ to $3 \times 10^{-22}$ cm$^2$/sr. As the signal coming from the molecules is about three times more intense than that associated with the nanotube, it is possible to deduce that the cross section of the collection of molecules under the beam is in the range of $10^{-22}$ to $10^{-21}$ cm$^2$/sr. The number of molecules in the exposed nanotubes under a beam having a diameter of 500 nm is approximated to be 455 per nanotube. Assuming that there is the equivalent of one nanotube completely filled with molecules, the cross section per molecule is between $2 \times 10^{-25}$ and $2 \times 10^{-24}$ cm$^2$/sr. Albeit approximate, this estimate is reasonable because the bundle contains, in reality, from 3 to 5 nanotubes, but these are partially filled by the molecules. It is noted that a cross section of $10^{-24}$ cm$^2$ per molecule is typical for a resonance process in Raman for dyes such as α-sexithiophene. The typical area of a molecule in this composite being 1.4 nm×4.47 nm/4=$1.57 \times 10^{-6}$ μm$^2$ (or $1.57 \times 10^{-14}$ cm$^2$), it is necessary to count about $10^{11}$-$10^{10}$ photons per molecule per nanotube to obtain a Raman signal.

This estimate of the cross section per molecule can be validated from measurements of laser power used to make the measurement. From earlier experiments, the laser light at a 514 nm wavelength and at 14.5 mW of power offers a power at the output of the 100× objective of about 2 μW at 100% and of about 1 μW at 50%. For the laser at 633 nm (13 mW), there was approximately 2 mW at the output of the 100× objective at 100% and about 1 mW at 50%. The numerical aperture of the 100× objective is 0.9 (angle of 65° or 1.13 sr) and the size of the spot is about 500 nm. The power in the case of FIG. 6 is 2 mW on a spot having a diameter of 500 nm (or an energy density of $\sim 10^6$ W/cm$^2$) and the exposure time for the spectrum is 30 seconds. This energy density corresponds therefore to a density of $7 \times 10^{17}$ photons μm$^{-2}$. (i.e., 30 seconds at $2 \times 10^{16}$ photons/s/μm$^2$). As the section of the nanotube under the beam is only 0.5 μm long and 1.4 nm wide, the total quantity of photons for the measurement of the spectrum is only $\sim 6 \times 10^{14}$ photons. The quantity of molecules is about 455, which gives a density of $10^{12}$ photons per molecule. This value is similar to an earlier estimate. Any difference may be attributed to the limited efficiency of the detector and to the loss of photons by the transfer optic.

b) Probes DPP@SWNT

Figure 7:
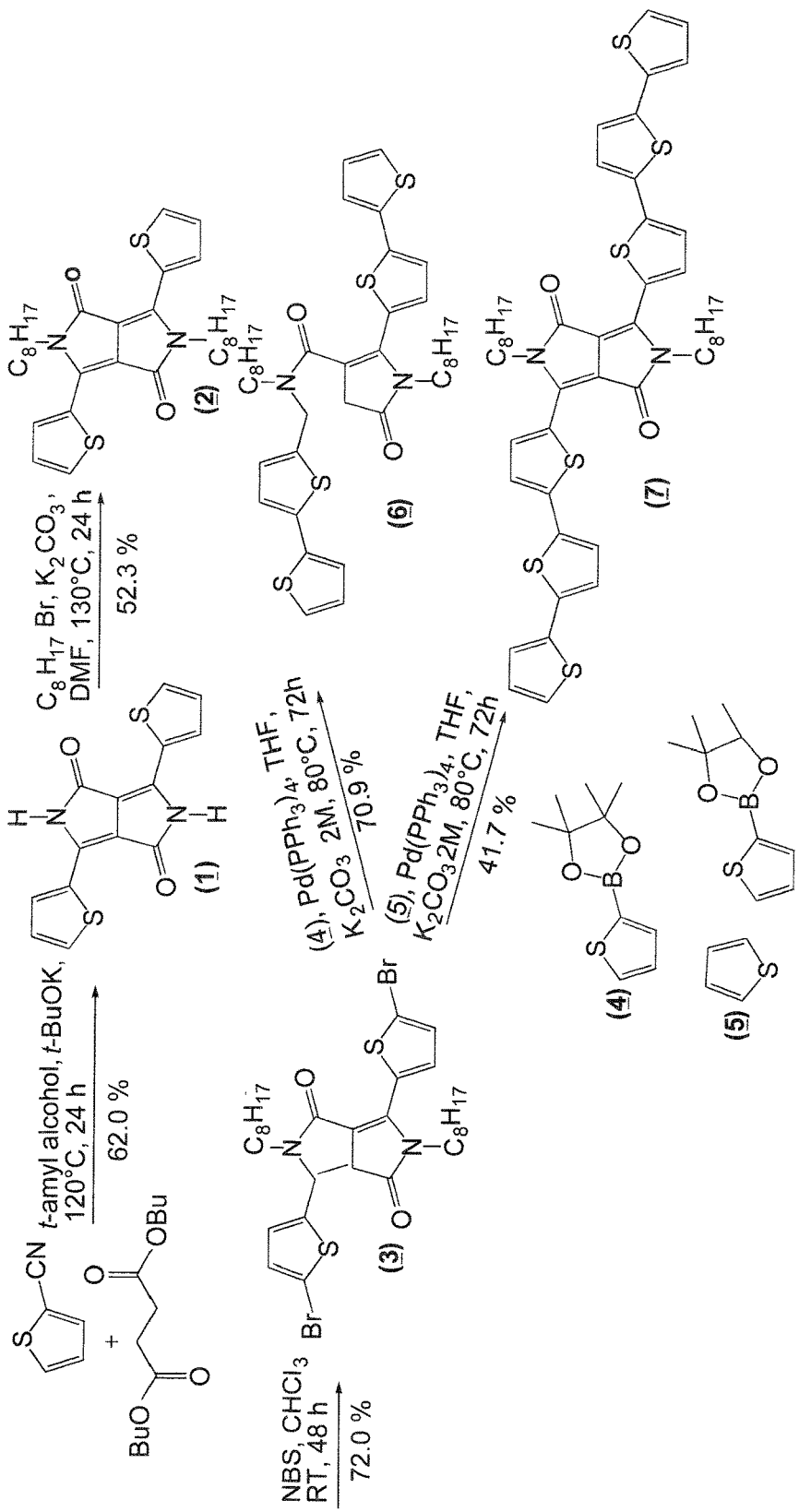
FIG. 7 shows a reaction diagram illustrating the steps for synthesizing DPP composites used for encapsulation in SWNT.

Other probes based on encapsulated oligothiophene were fabricated so as to investigate the fabrication of active probe at other resonance energies. The inventors prepared DPP composite probes that, as indicated below, allow an adjustment of the resonance energy at various positions in the visible spectrum. DPP (DPP1, DPP2 and DPP3) are analogs to polythiophene that offer interesting resonances in the wavelength range from red (near 633 nm) to blue (514 nm). These molecules offer a great flexibility of synthesis. The reaction diagram shown in FIG. 7 illustrates the steps for synthesizing DPP composites used for encapsulation in SWNT. In the diagram, DPP2 is the compound (6) and DPP3 is the compound (7).

The preparation of these DPP@SWNT probes involves first cleaning and opening carbon nanotubes in the manner described above. For the encapsulation, 2 mg of cleaned and opened SWNT are dispersed in 20 ml of DMF by sonication for thirty minutes, after which 10 mg of DPP dye is added and the solution is treated with ultrasound for another five minutes. The solution is heated to reflux overnight in a nitrogen atmosphere. The sample is harvested by filtration after ten washes with THF with gentle sonication for three minutes between the washes to disperse the tubes following a filtration and ten other similar washes with DMF. The functionalization of these composites with the group R proceeds according to the protocol described above.

Figure 8A:
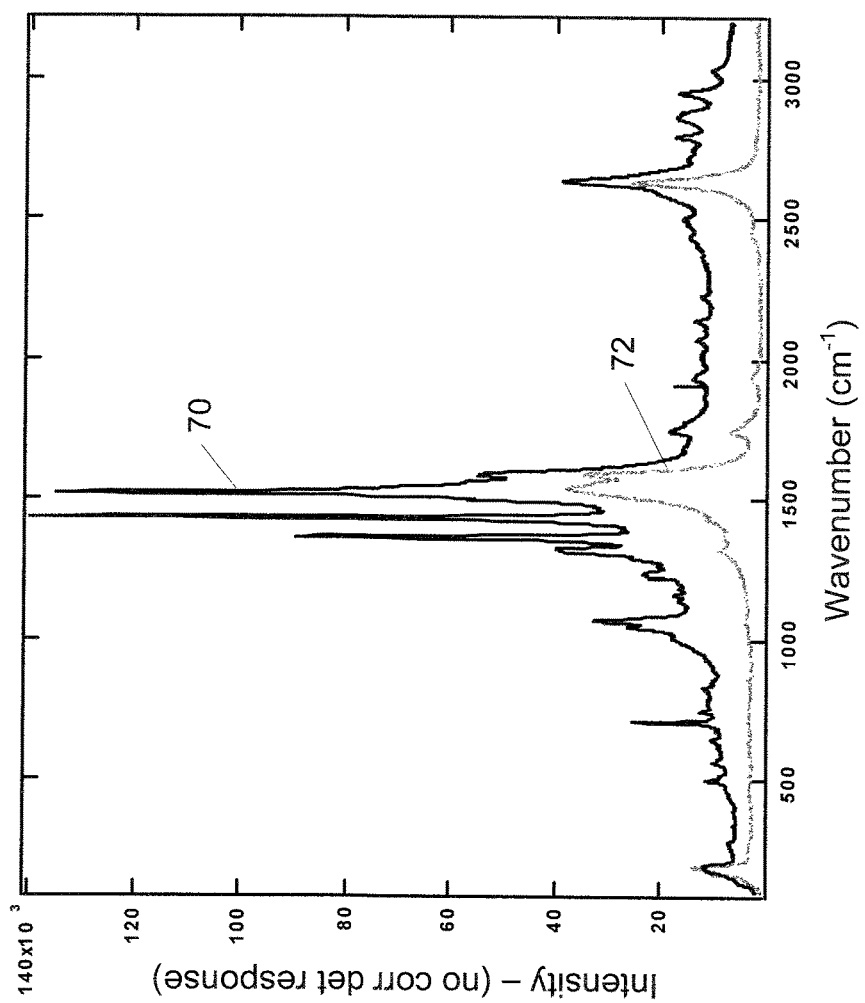
FIG. 8A shows a Raman spectrum of DPP2 molecules encapsulated in SWNT (DPP2@SWNT) measured at 633 nm and the spectrum of a preparation using a carbon nanotube sample that did not undergo the nanotube opening step. This Raman control test allows one to verify the fabrication protocol of the probe and to confirm the encapsulation of molecules inside the carbon nanotube.
Figure 8B:
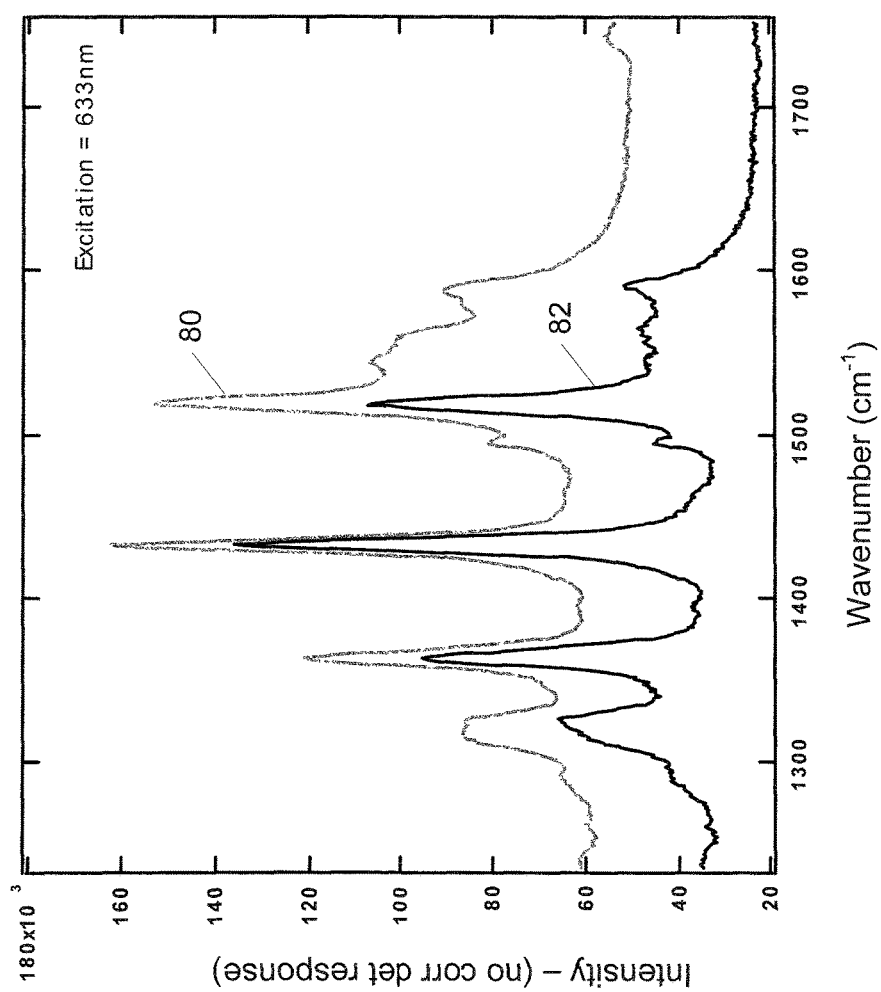
FIG. 8B shows the Raman spectra during the fabrication steps of the DPP2@SWNT probe just after the encapsulation and after the functionalization with a chemical grouping R. The Raman spectra are measured at 633 nm.

The fabrication of probes DPP3@SWNT, DPP2@SWNT and DPP1 @SWNT was done in steps. For each step, the Raman spectra were measured. FIGS. 8A and 8B show examples of Raman spectra measured during the synthesis steps for the probe DPP2@SWNT. In FIG. 8A is shown the spectra at 633 nm with and without the step of opening of the SWNTs. In the figure, reference numeral 70 indicates the DPP2 spectrum with the SWNT opened, and reference numeral 72 indicates the spectrum with the SWNT unopened, which contains no DPP signal and only SWNT Raman peaks.

It is noted that these spectra show clearly that the opening and cleaning step is essential to obtain a strong signal of the DPP molecules. The final step of functionalization with the chemical group R (here R=bromophenyl), as shown in FIG. 8B, demonstrates that the Raman spectrum remains almost identical to that measured before this step. In this figure, the DPP2@SWNT spectrum without the chemical group R is identified by reference numeral 80, while the DPP2@SWNT spectrum with the group R is identified by reference numeral 82.

Figure 9:
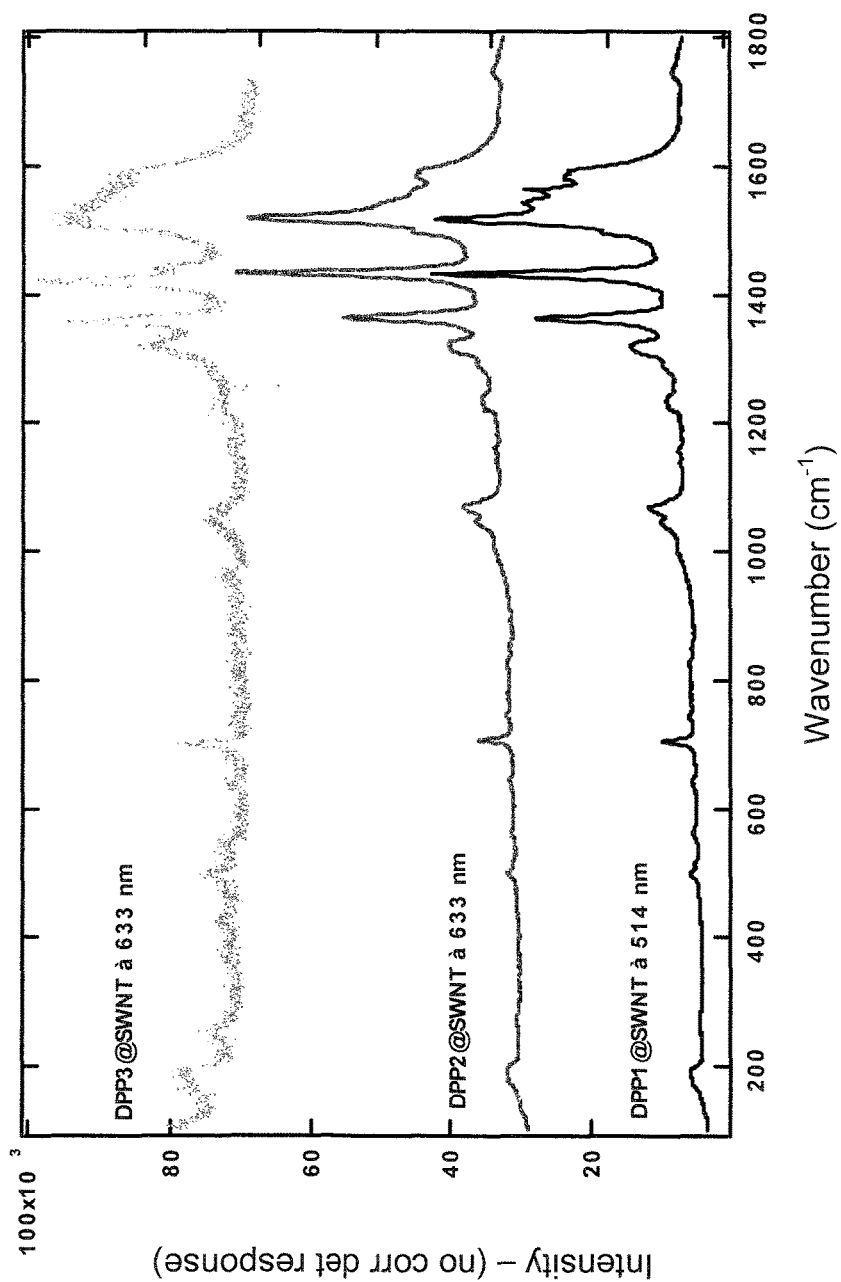
FIG. 9 shows the Raman spectra of DPP3 molecules encapsulated in carbon nanotube (DPP3@SWNT) and DPP2@SWNT at 633 nm, and of the probe composed of DPP1 encapsulated in carbon nanotubes (DPP1@SWNT) at 514 nm.

This experiment shows that the covalent reaction on the external surface of the SWNT causes little or no modification of the Raman spectrum. FIG. 9 shows the Raman spectra of three probes DPP3@SWNT, DPP2@SWNT and DPP1 @SWNT at excitation wavelengths of 633 nm, 633 nm and 514 nm, respectively. While the functionalization does not affect the Raman response, nevertheless, it is clearly illustrated when one compares the dispersion or solubility of probes in a solvent. A non-functionalized probe is insoluble in a liquid such as DMF and forms an insoluble precipitate. A probe functionalized by the chemical group R disperses easily in a solvent and forms a stable suspension without aggregation. Moreover, a spectroscopic measurement of photoemission X (by XPS) allows confirmation that the attachment of the chemical group R is successful.

Example 2: Encapsulated Raman Scattering Probes with Commercial Molecules

Multiple capsule probes can be made using commercial molecules. The choice of a Raman-active molecule is made based on the Raman resonance energy and the spectral characteristics necessary for a given application. There is a wide variety of different molecules available, and the inventors have worked with such molecules as methylene violet B and diethylthiodicarbocyanine iodide (DTDCI).

a) Methylene Violet B@SWNT Probes

Capsule probes prepared with methylene violet B have been shown to provide a good response in Raman scattering. Methylene violet B possesses the following structure:

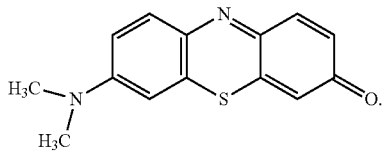 [SMILES: CN(C)c1ccc2nc3ccc(=O)cc-3sc2c1]

The process of fabrication follows the general steps described. For the encapsulation step, an abundance of the SWNT and the methylene violet B are dispersed in heptane and the suspension is treated with ultrasound for about two minutes. The suspension is then agitated overnight to reflux, and is subsequently purified by successive cleanings with DMF. This step is terminated when the filtrate remains only very slightly colored or when the Raman spectra recorded before and after the last washing session are equivalent.

Figure 10:
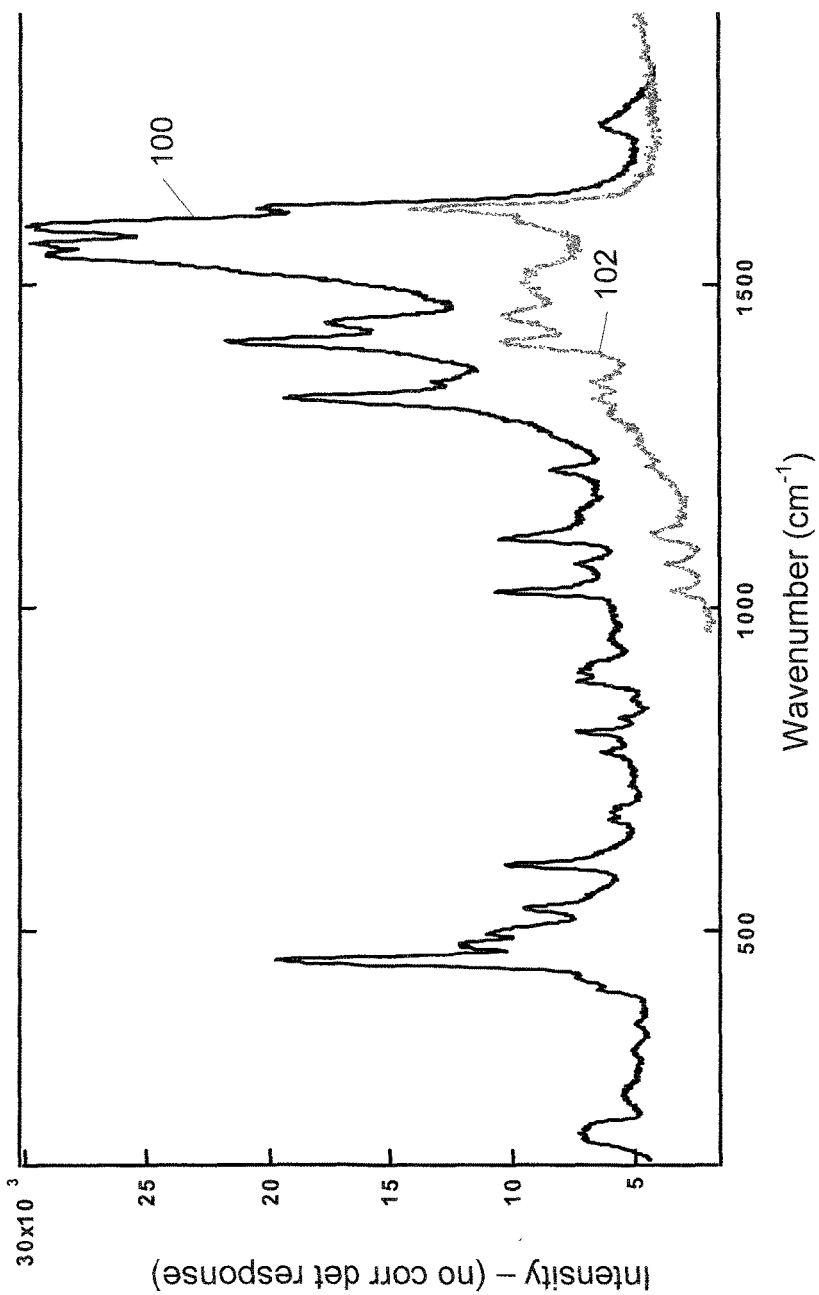
FIG. 10 shows the Raman spectrum of the methylene violet molecules encapsulated in carbon nanotube (Violet B@SWNT) measured at 633 nm, with the Raman spectrum of methylene violet B in powder form and measured at 488 nm.

An example of a Raman spectrum at 633 nm of the methylene violet B@SWNT probe obtained after the synthesis is shown in FIG. 10 and indicated by reference numeral 100. The Raman signature of the probe is also compared with that of methylene violet B powder, for which the spectrum is also shown in FIG. 10 and indicated by reference numeral 102. Differences between the spectra are noticeable, particularly in the region surrounding 1500 $cm^{-1}$. These differences come from the encapsulation of the molecules in the SWNT probe.

b) DTDCI@SWNT Probes

The fabrication of probes with diethylthiodicarbocyanine iodide (DTDCI) also worked well. These probes were also prepared according to the general protocol described above. The structure of DTDCI illustrated below is that of a conjugated linear molecule that offers a good polarizability and, therefore, good response in Raman diffusion in the visible range.

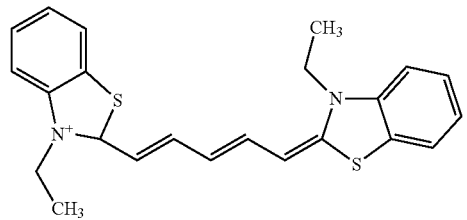 [SMILES: CCN1\C(=C/C=C/C=C/C2Sc3ccccc3[NH+]2CC)Sc2ccccc21]

For the encapsulation step, the SWNT are dispersed with an abundance of DTDCI in water, followed by an ultrasonic treatment for about 15 minutes. The solution is then brought to reflux under agitation for twenty hours. Multiple cleanings using DMF were done until complete extraction of the non-encapsulated dye was achieved (i.e., until the filtrate is uncolored).

Figure 11:
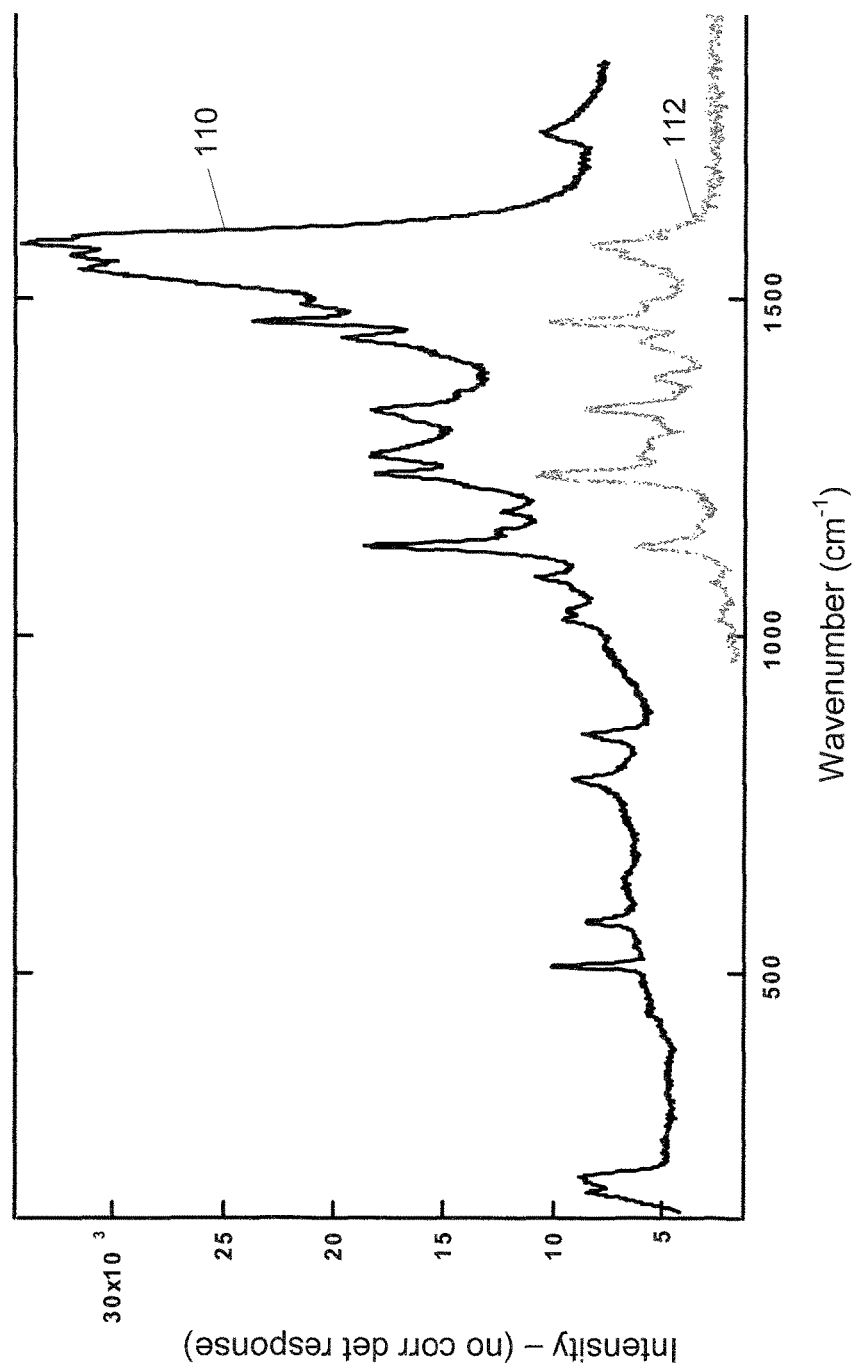
FIG. 11 shows the Raman spectrum of the DTDCI molecules encapsulated in carbon nanotubes (DTDCI@SWNT) measured at 633 nm and compares it with the Raman spectrum of DTDCI in powder form and measured at 488 nm.

The Raman spectrum at 633 nm of the DTDCI@SWNT probe obtained after the synthesis is shown in FIG. 11 and is indicated by reference numeral 110. The Raman spectrum of the probe is also compared with that of DTDCI powder, which is also shown in FIG. 11 and indicated by the reference numeral 112. The differences between the two spectra are noticeable. These differences come from the encapsulation of the molecules in the SWNT.

Example 3: Toluidine Blue-DWNT Probes (External Dye Attachment)

An example of a capsule probe such as that shown in FIG. 1B was achieved using toluidine blue as the Raman-active molecule. For this probe, the Raman-active dye is chemically attached by a covalent reaction to the exterior of the nanotubes and, more particularly, to the external surface of the capsule.

The fabrication method uses one variation of the general method presented above. Because the step of encapsulation is not necessary for these probes, that step is omitted, and the process goes directly to the chemical attachment of the dye to the capsule. For the toluiding blue-DWNT probe, one part double wall nanotubes (DWNT) and four parts toluidine blue are placed in a round-bottom flask. The flask is purged with nitrogen and heated to 130° C. Thirty parts of isoamylnitrite are then added to the mixture and the reaction proceeds for 24 hours under vigorous agitation. The residue that contains toluidine blue-DWNT is rinsed with water twice and washed subsequently multiple times with DMF until the free dye is completely removed (free toluidine blue being very soluble in DMF). The washing is done by an ultrasonic treatment for 10 minutes of the residue of the reaction in the DMF. The product is then harvested by filtration and drying with THF.

A variation of this reaction which gives the same result uses a reaction in liquid phase instead of the solid state. The procedure in the liquid phase is the same except that the quantity of isoamylnitrite is 45 parts (instead of 30) and the anhydrous DMF is added to the medium at the proportion of 200 parts. The diagram of the insertion reaction of the toluidine blue by external attachment to the nanotubes is shown in FIG. 12A (where "CNT" represents the carbon nanotubes, and "DMF (anhydre)" refers to the anhydrous DMF).

Figure 12B:
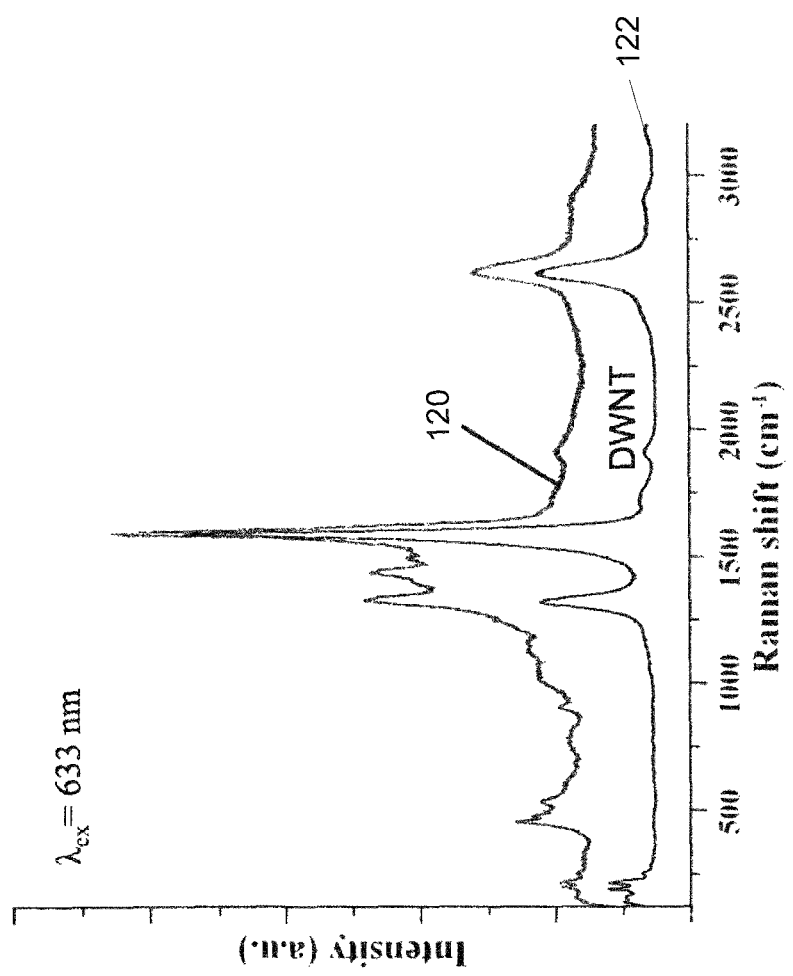
FIG. 12B shows the spectrum of the probe Toluidine Blue attached by covalent bond to the external surface of double wall nanotubes (DWNT). The bottom spectrum is that of DWNT in the absence of encapsulation and chemical functionalization.

The spectrum at 633 nm of the toluidine blue-DWNT probe, obtained after the solid synthesis, is shown in FIG. 12B and is indicated by reference numeral 120. The Raman spectrum of the probe is compared with that of the double wall nanotubes (DWNT), which is also shown in FIG. 12B and indicated by reference numeral 122. Additional bands around 500 and 1400 cm$^{-1}$ are noticeable in the spectrum of toluidine blue-DWNT. These bands come from a Raman signal of toluidine blue molecules attached chemically to the DWNT.

Detailed Investigation of α-Sexithiophene Probes

Figure 13:
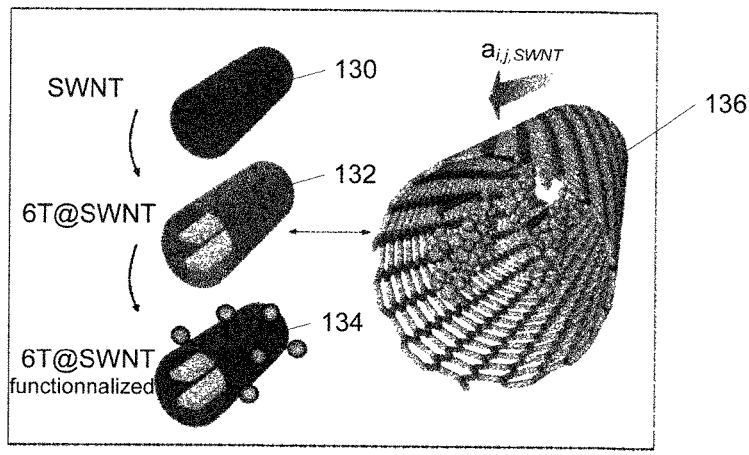
FIG. 13 is a schematic view of the steps of preparation for a 6T@SWNT probe according to an embodiment of the invention.

In another experiment conducted by the inventors, Raman probes were produced that consisted of α-sexithiophenes (6T) encapsulated within phenyl-functionalized SWNT (6T@f-SWNT). A detailed study with Raman was carried out in situ at each step of the preparation procedure. The general steps of this procedure are illustrated schematically in FIG. 13. In a first step, the nanotubes 130 were processed by acid and ultrasound and encapsulated in a liquid phase with 6T molecules. The resulting 6T@SWNT 132 were then functionalized with either iodophenyl or bromophenyl groups by covalent addition using diazonium salts. This procedure yields the 6T@f-SWNT product 134 with the phenyl grafts, as indicated in the figure. Shown at 136 in FIG. 13 is a more detailed illustration of the 6T aligned inside a nanotube. The arrow shown in the figure indicates the directional Raman polarizability of the molecules.

In preparing the 6T@f-SWNT probes, only reagent grade solvents were used. 4-bromobenzenediazonium tetrafluoroborate (96%, Aldrich), 4-aminopropyltriethoxysilane (APTES) (99%, Aldrich), isopentyl nitrite (96%, Aldrich), and the α-sexithiophene (Aldrich) were used as received. 4-Iodoaniline (98%, Aldrich) was recrystallized from hexanes before use. The SWNT were produced by laser ablation.

For the encapsulation of α-sexithiophene in SWNT (6T@SWNT), the SWNT first were purified using concentrated nitric acid wet chemical oxidation and cut by exposing the SWNT to piranha solution (3:1 conc. $H_2SO_4/H_2O_2$) for three hours. The SWNT were filtered on a PTFE filter (1.2 µm pore size), and were thoroughly washed with water. 55 mg of the nanotube residue was then dispersed in DMF, filtered, dispersed in THF, filtered, and rinsed with toluene. 12 mg of 6T was thereafter added to 10 mL of toluene and sonicated for five minutes. The buckypaper obtained by filtration was added to the 6T solution, and sonicated for two minutes and refluxed at 115° C. for 48 hours. The encapsulated SWNT were filtered on a PTFE filter (0.45 µm), and dispersed in 15 mL DMF. Dispersion and filtration of the nanotubes was repeated five times to removed free 6T molecules. The resulting buckypaper of 6T@SWNT was subsequently characterized by Raman spectroscopy.

The iodophenyl functionalization of 6T@SWNT (6T@f-SWNT) was done on 1 mg of 6T@SWNT and 75 mg of iodoaniline, which were purged in nitrogen followed by the addition of 20 µL of isopentylnitrate. The reaction was heated to 80° C. for three hours, and the mixture was then diluted in 25 mL of DMF and filtered. The 6T@f-SWNT were washed in DMF until the filtrate was free of iodoaniline, as measured by thin layer chromatography.

An aminopropyltriethoxysilane substrate (APTES) was formed on a patterned $SiO_2$/Si substrate. Preparation of this substrate began with a substrate of silicon having a 100 nm oxide ($SiO_2$/Si). An electrode pattern was created using standard photolithography followed by e-beam evaporation of titanium (0.5 nm) and palladium (25 nm). This pattern was used to identify individual nanotubes on the substrate and allowed location of the same structure with the Raman after each modification. A substrate cleaning procedure consisted of successive sonication of five minutes each in acetone and isopropanol (IPA). The substrates were then placed in a glass desiccator and vacuum dried for at least ten minutes. The substrates were then placed on glass slides suspended above a small crystallization dish containing one milliliter of APTES. The desiccator was vacuum pumped for one minute and the chamber was sealed for an additional thirty seconds. Finally, the APTES layer was annealed in air for twenty minutes at about 100° C. in a conventional oven.

The SWNT were then deposited on the APTES patterned substrate. Purified SWNT were suspended in N,N-dimethylformamide (DMF) and diluted as needed. The SWNT were spin-coated onto the APTES substrate at a speed of 7000 rpm from the DMF suspension to obtain about 1 nanotube/3 µm$^2$.

To perform the encapsulation yielding the 6T@SWNT, the SWNT on the substrate were dipped in DMF, THF and toluene to remove water. 12 mg of 6T was then mixed with 5 mL of toluene in a round bottom flask and sonicated for five minutes. The substrate covered with SWNT was gently placed into a flask equipped with a condenser and the solution was refluxed at 115° C. for 24-48 hours. Residual 6T was removed from the surface by first sonicating in fresh toluene and sonicating in DMF. The sample was then rinsed with IPA and nitrogen-dried before characterization by atomic force microscopy (AMF) and Raman spectroscopy.

The functionalization of the 6T@SWNT to give 6T@f-SWNT started with a 2 mM 4-bromobenzenediazoniumtetrafluoroborate prepared with 20 mL of degassed milliQ water (pH ~10). 6T@SWNT was then placed into the aqueous salty solution for ten minutes and rinsed in water and IPA, and dried using a nitrogen flow.

To create a layer of 6T@SWNT in a cross pattern (the results of which are discussed below in conjunction with FIG. 16), APTES was deposited on a $SiO_2$ substrate as described above. A suspension of 1 mg/mL of 6T@SWNT in DMF was then prepared by sonicating for 10 min. The APTES substrate was immersed into the 6T@SWNT dispersion for thirty minutes at room temperature, and was then rinsed with DMF before being immersed in hot DMF for two minutes. The nanotube-covered substrate was rinsed with IPA and blow dried with nitrogen. A layer of Shipley S1805 photoresist was then spin-coated onto the nanotube-covered substrate, and a cross pattern was defined using photolithography. The unprotected regions were removed by an oxygen reactive ion etch (30 s, 125 mTorr, 80 mW/cm$^2$), and the substrate was plunged into remover to reveal a cross pattern of 6T@SWNT. This pattern was then characterized using SEM images and Raman spectroscopy.

Measurement of the 6T@f-SWNT Probes

The experimental results shown in FIGS. 14A-16 were acquired on individualized SWNT deposited on an oxidized silicon substrate, on a sub-monolayer of 6T@SWNT on an oxidized silicon substrate and patterned by optical lithography in a cross pattern or on bulk 6T@f-SWNT dispersed in an inorganic oil. These spectra were recorded at each step of the procedure using absorption and Raman spectroscopy. The structures of the probes were also investigated using AFM and SEM.

The AFM images were produced using a Dimension 3100 scanning probe microscope equipped with a Nanoscope IV controller and a quadrex extender module. Height images were acquired using intermittent-contact mode using silicon probes of nominal spring constants of 42 Nm$^{-1}$, a resonance frequency of ~320 Hz, and a tip radius curvature <10 nm.

The Raman spectrometer used is a custom-built instrument with three different excitation laser lines (2.54, 2.45, 1.94 eV), a 100× objective and a nitrogen cooled charged-coupled device camera (JY Symphony). The sample plane was equipped with a 3-axis piezoelectric displacement stage. The laser power on the sample was ~95 µW µm$^{-2}$. Spectral region probe was between 1200-1700 cm$^{-1}$ in the D and G regions of the SWNT with a precision of ±1 cm$^{-1}$. The Raman mapping was performed with 1 µm steps in the X and Y axis. Each point was integrated for five seconds with a laser power of 300 µW µm$^{-2}$.

Figure 14A:
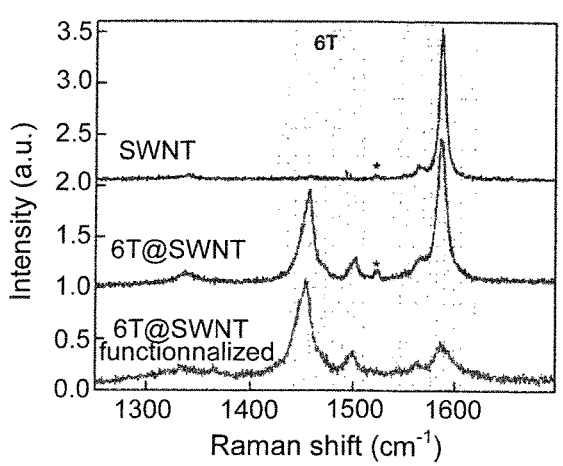
FIGS. 14A and 14B are graphical views, respectively, of the Raman spectrum and the absorption spectra of 6T and the probes in oil such as that of FIG. 13 taken at different stages in its preparation.
Figure 14B:
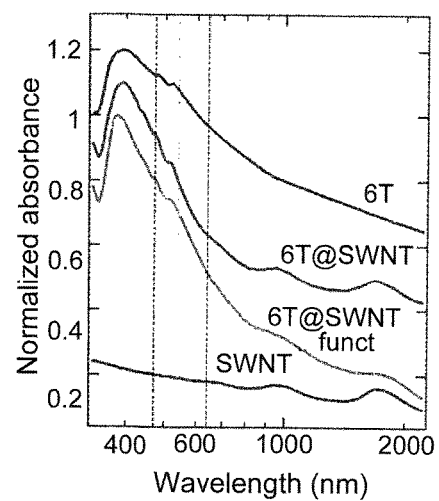

Absorption spectra of the SWNT, 6T@SWNT and 6T@f-SWNT bulk dispersed in inorganic oil are shown in FIG. 14B. As shown, the absorption of the 6T is intense and structured in the 350-700 nm region. The 6T@SWNT has an absorption spectrum that combines the 6T and SWNT absorption features with no significant shift in the resonant absorption peaks. The 6T@f-SWNT shows a spectrum that is similar to the 6T@SWNT except that the absorption of the SWNT is weaker because of the grafting of the phenyl groups onto the SWNT sidewalls.

For the Raman spectrum shown in FIG. 14A, an individual and isolated SWNT was previously located on the oxidized silicon substrate and identified by AFM and Raman. Its apparent height in AFM is 1.2 nm, which corresponds to the diameter of an individual nanotube. For each step of the procedure, Raman spectra in FIG. 14A were taken at the same location and using the same polarization conditions. Before encapsulation (top spectrum), the shape of the Raman G mode at ~1590 cm$^{-1}$ confirms the presence of a semiconducting SWNT. The presence of a single RBM mode (not shown) is consistent with a signal coming from an individual SWNT. After encapsulation (middle spectrum), the Raman peaks characteristic of 6T molecules appeared strong and clear in the spectra of 6T@SWNT. The most intense peak of the 6T at 1450 cm$^{-1}$ is assigned to the main component of the C=C stretching mode propagating along the main axis of the molecule. The presence of this Raman mode unambiguously reveals the presence of 6T molecules. An inspection of the area around the 6T@SWNT indicated no signal, which implies that the molecular signal is only from the 6T@SWNT structure, not from other 6T molecules adsorbed on the surface. The Raman spectra taken after the bromophenyl functionalization step on the individual 6T@SWNT is shown in the bottom spectrum of FIG. 14A. The intensity of the 6T peak is preserved whereas the G mode of the SWNT at ~1590 cm$^{-1}$ decreases in intensity.

The appearance of a defect mode, called the D-mode, of the SWNT at ~1330 cm$^{-1}$ indicates that there is an interaction between the molecules (6T and grafts) and the SWNT. The change of the SWNT modes in the spectrum and the absence of any change for the 6T signal proves that the SWNT has been functionalized with the bromophenyl adducts and that the 6T are located inside the nanotube.

Figures 15A, 15B, 15C:
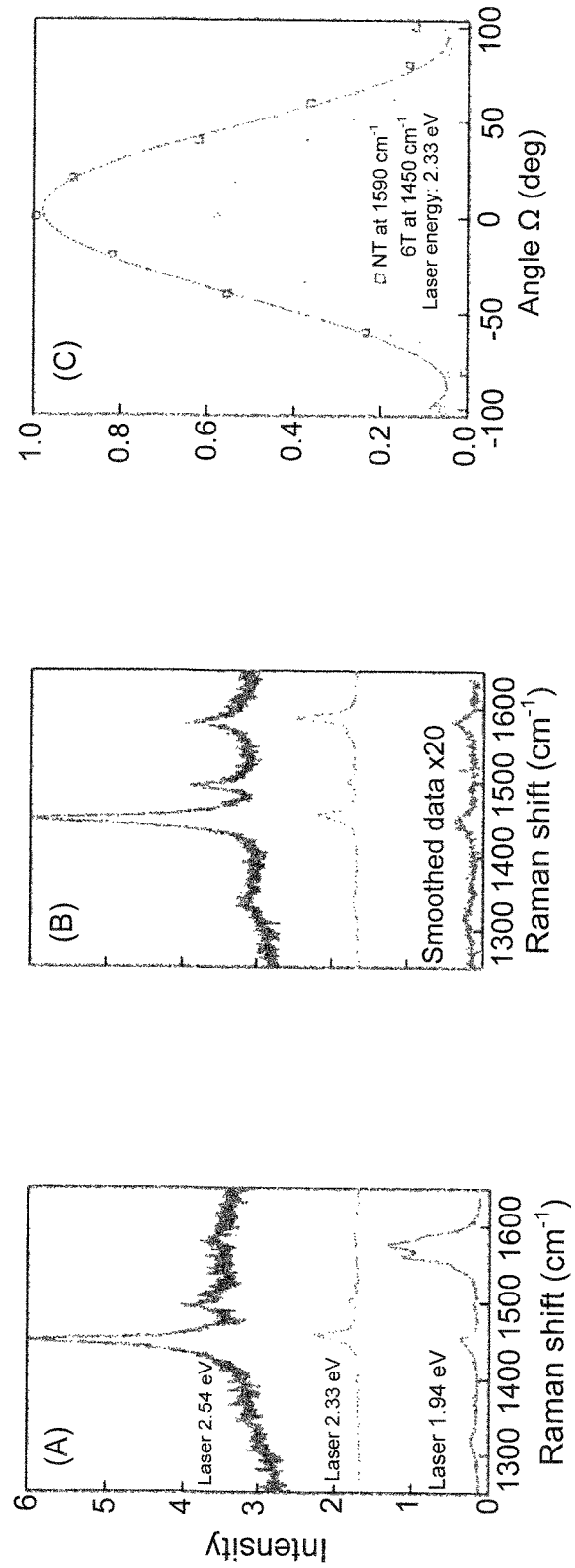
FIGS. 15A and 15B are graphical views, respectively, of the Raman spectra of a metallic 6T@SWNT probe and a semiconducting 6T@SWNT probe at three different laser energies.
FIG. 15C is a graphical view of the variation of intensity with polarization for two Raman peaks of a semiconducting 6T@SWNT probe. The inset shows an atomic force microscopy image of the 6T@SWNT with a description of the polarization angle.

In another set of experiments, two individual 6T@SWNT deposited on an oxidized silicon substrate were first located using micro Raman spectroscopy and AFM imaging (FIGS. 15A-15B). The Raman spectrum associated with each SWNT capsule presents distinct resonances with excitation energy, which indicates that one is metallic (FIG. 15A) and the other is semiconducting (FIG. 15B). For our laser ablation SWNT sample, such identification is possible because only metallic SWNT are resonant in Raman at 1.94 eV (FIG. 15A) whereas semiconducting SWNT are resonant only at 2.33 eV and 2.54 eV (FIG. 15B). At 2.33 and 2.54 eV excitations, the individual metallic 6T@SWNT has an intense 6T peak at 1460 cm$^{-1}$ and there is almost no signal from the SWNT capsule. Thus, the SWNT is out of resonance while the 6T is clearly in resonance, which is consistent with the absorption spectra in FIG. 14B. At 1.94 eV excitation, the opposite is observed: The 6T signal is weak and the SWNT is strong. The Raman signals of the SWNT and 6T are therefore uncorrelated from each other and simply follow the resonance pattern, as in the absorption spectrum. Moreover, one can clearly see that the presence of a SWNT resonance does not significantly contribute to the enhancement of the 6T Raman signal. For the individual semiconducting 6T@SWNT (FIG. 15B), both 6T and SWNT show Raman peaks at 2.54 and 2.33 eV and no signal at 1.94 eV excitation. This coincidence arises from a spectral overlap of their respective resonances. For both metallic and semiconducting 6T@SWNT, the intensity of the 6T signal follows only the absorption profiles of the molecules. Whether the SWNT capsule is metallic or semiconducting, functionalized or not, have therefore no influence on the 6T signal. Lastly, the spectra indicate little or no fluorescence signal from the Raman probe. The structure is therefore active to suppress the usual fluorescence background from the dye molecules. These characteristics are ideal for Raman imaging and tagging applications.

Polarization experiments were done on the individual semiconducting 6T@SWNT. The polarization plot in FIG. 15C indicates the Raman signal of the 6T (1450 cm$^{-1}$) and individual SWNT (1590 cm$^{-1}$) versus laser polarization at 2.33 eV are directly correlated. The polarization angle, θ, is defined by the angle between the tube axis and the polarization vector of the light (inset FIG. 15C). The cos$^2$θ dependency of the polarization demonstrates that the 6T molecules are dipole active and that they are well aligned along the tube. This property of the Raman probe shows one advantage of an encapsulation of the molecules. Both the polarization results and the effect of the covalent functionalization of the SWNT capsules clearly demonstrate that the SWNT protects and aligns the 6T molecules. The end result is indicative of a strongly polarizable Raman probe giving a strong anisotropic signal.

The unique structural properties of the Raman probe appear to be at the origin of the large enhancement factor seen in Raman scattering of the molecules encapsulated inside the SWNT. An analysis of the Raman cross section of the individual SWNT, as done previously with the 6T@SWNT bundle in FIG. 6, reveals that the cross section is also ~10$^{-21}$ cm$^2$/sr for the Raman probe at 1460 cm$^{-1}$, which is the wavenumber of the 6T specific signal. Assuming that a maximum of 455 molecules is present, the cross section per molecule is ~$10^{-24}$ cm$^2$/sr. This value is consistent with the cross section of similar Raman dyes in resonance. It shows that the Raman probe provides the best conditions to take advantage of resonant Raman effects of dye molecules. Considering an area per molecule of (1.4 nm×4.47 nm)/4=1.57×$10^{-14}$ cm$^2$, such cross section implies that roughly $10^{11}$-$10^{10}$ photons are enough to detect the Raman signal of the probe. This is quite reasonable considering the typical laser powers currently available (~$10^{14}$ photon s$^{-1}$ cm$^{-2}$ at 45 μW/cm$^2$ for 633 nm wavelength). The Raman cross section of the probe is therefore well-adapted for Raman imaging. This is demonstrated in the image of FIGS. 16A-16C. A layer of 6T@SWNT was patterned on the SiO$_2$/Si substrate and imaged using SEM (FIG. 16A) and Raman (FIG. 16B) mapping. Both images nicely overlap as shown in FIG. 16C. This Raman image took only five seconds per pixel to acquire at 300 μW/cm$^2$ laser power. Thus, this demonstration provides an example of possible application with the Raman probe in Raman imaging and molecular labeling.

The invention claimed is:

1. A method of performing a Raman investigation of a sample, the method comprising:
    attaching a Raman scattering probe to a target material of interest within the sample, the Raman scattering probe comprising an elongated capsule of nanometric size and multiple Raman-active molecules coupled to the elongated capsule and aligned along said elongated capsule, the Raman scattering probe further comprising at least one functionalization chemical group attached to an exterior of the elongated capsule and forming a bond with the target material;
    illuminating the sample with an excitation light beam at an excitation wavelength such that said Raman-active molecules collectively exhibit a Raman scattering response at a shifted wavelength, said Raman scattering response being stronger than fluorescence noise from the Raman-active molecules at said shifted wavelength; and
    detecting light resulting from the Raman scattering response.

2. A method according to claim 1, wherein the capsule comprises at least one nanotube.

3. A method according to claim 1, wherein the Raman-active molecules are encapsulated within the capsule.

4. A method according to claim 1, wherein the Raman-active molecules are attached to an external surface of the capsule.

5. A method according to claim 1, wherein the Raman-active molecules are attached to the functionalization chemical group.

6. A method according to claim 1, wherein the Raman investigation comprises Raman spectroscopy.

7. A method according to claim 1, wherein the Raman investigation comprises Raman imaging.

8. A method of performing a Raman investigation of a sample, comprising:
    a) providing a Raman scattering probe responsive to light at an excitation wavelength, comprising:
        an elongated capsule of nanometric size;
        multiple Raman-active molecules coupled to the capsule, said Raman-active molecules collectively exhibiting a Raman scattering response at a shifted wavelength when the probe is illuminated by the light at the excitation wavelength, said Raman-active molecules being aligned along the elongated capsule such that said Raman scattering response is stronger than fluorescence noise from the Raman-active molecules at said shifted wavelength; and
        at least one functionalization chemical group that is attached to an exterior of the elongated capsule and that enables a connection between the capsule and a target material;
    b) attaching the Raman scattering probe to a target material of interest within the sample via said at least one functionalization group;
    c) illuminating the sample with an excitation light beam at the excitation wavelength; and
    d) detecting light at the shifted wavelength resulting from the Raman scattering response.

9. A method according to claim 8, wherein the elongated capsule comprises at least one nanotube in which are encapsulated the Raman-active molecules.

10. A method according to claim 8, wherein the Raman investigation comprises Raman spectroscopy.

11. A method according to claim 8, wherein the Raman investigation comprises Raman imaging.

* * * * *